US006663590B2

United States Patent
Blatter

(10) Patent No.: US 6,663,590 B2
(45) Date of Patent: *Dec. 16, 2003

(54) VASCULAR OCCLUSAL BALLOONS AND RELATED VASCULAR ACCESS DEVICES AND SYSTEMS

(75) Inventor: Duane D. Blatter, Salt Lake City, UT (US)

(73) Assignee: Integrated Vascular Interventional Technologies, L.C. (IVIT, LC), Salt Lake City, UT (US)

( * ) Notice: Subject to any disclaimer, the term of this patent is extended or adjusted under 35 U.S.C. 154(b) by 20 days.

This patent is subject to a terminal disclaimer.

(21) Appl. No.: 09/760,322

(22) Filed: Jan. 11, 2001

(65) Prior Publication Data

US 2001/0007931 A1 Jul. 12, 2001

Related U.S. Application Data

(63) Continuation-in-part of application No. 09/480,964, filed on Jan. 11, 2000, and a continuation-in-part of application No. 09/481,283, filed on Jan. 11, 2000.

(51) Int. Cl.[7] .......................... A61M 29/00; A61M 5/00; A61F 2/06
(52) U.S. Cl. ..................... 604/103.01; 604/9; 623/1.24; 623/1.42
(58) Field of Search ....................... 604/890.1, 8, 891.1, 604/9, 96.01, 97.02, 103.01, 103.05, 167.01–167.03, 181, 183, 288.01–288.04; 623/1.24, 1.42, 23.64, 23.68

(56) References Cited

U.S. PATENT DOCUMENTS

| 3,392,722 A | 7/1968 | Jorgensen ..................... 128/1 |
| 3,395,710 A | 8/1968 | Stratton et al. ............. 128/350 |
| 3,826,257 A | 7/1974 | Buselmeier |
| 3,991,756 A | 11/1976 | Synder |
| 4,122,858 A | 10/1978 | Schiff |
| 4,301,797 A | 11/1981 | Pollack |
| 4,318,401 A | 3/1982 | Zimmerman |
| 4,370,983 A | 2/1983 | Lichtenstein |
| 4,623,348 A | 11/1986 | Feit |
| 4,655,771 A | 4/1987 | Wallsten ..................... 623/1.22 |
| 4,819,637 A | 4/1989 | Dormandy, Jr. et al. .... 128/325 |
| 4,846,186 A | 7/1989 | Box et al. .................... 128/657 |

(List continued on next page.)

FOREIGN PATENT DOCUMENTS

| WO | WO 98/19629 | 5/1998 | ............. A61F/2/06 |
| WO | WO 98/19634 | 5/1998 | ............. A61F/2/06 |

OTHER PUBLICATIONS

Lycos, Your Personal Internet Guide, Apheresis, located at http://infoplease.lycos.com/ipd/A0321273.html, 2 pgs, printed Dec. 17, 1999.

Clark Biocompatible Hemoperfusion System and Block Cutter, *Some Other Products from Clark Research, Clark® Biocompatible Hemoperfusion*, located at http://www.clarkrd.com/crd_other2.htm, 2 pgs., printed Dec. 17, 1999.

(List continued on next page.)

*Primary Examiner*—Brian L. Casler
*Assistant Examiner*—Catherine Serke
(74) *Attorney, Agent, or Firm*—Stoel Rives, LLP

(57) ABSTRACT

Vascular access systems and devices for facilitating repeated access to a blood vessel for the external treatment of blood, such as dialysis, and in intra-venous administration of medicines, such as heparin, for extended periods of time. The vascular access systems comprise an anastomosis graft vessel, an occlusal balloon, and a port device for accessing the occlusal balloon. Occlusal balloons can be nonpermeable or permeable to drive an osmotic gradient and to deliver agents, such as heparin, into the blood stream. In addition, occlusal balloons can adopt a distended and a collapsed configuration, the latter allowing for blood flow through the anastomosis graft vessel.

37 Claims, 16 Drawing Sheets

U.S. PATENT DOCUMENTS

| | | | |
|---|---|---|---|
| 5,092,841 A | 3/1992 | Spears | |
| 5,102,402 A | 4/1992 | Dror et al. | |
| 5,211,683 A | 5/1993 | Maginot | |
| 5,290,306 A | 3/1994 | Trotta et al. | 606/194 |
| 5,304,220 A | 4/1994 | Maginot | |
| 5,411,475 A | 5/1995 | Atala et al. | 604/54 |
| 5,417,657 A | 5/1995 | Hauer | |
| 5,443,497 A | 8/1995 | Venbrux | 623/1.13 |
| 5,456,712 A | 10/1995 | Maginot | 623/1 |
| 5,458,568 A * | 10/1995 | Racchini et al. | 604/103.01 |
| 5,478,320 A | 12/1995 | Trotta | |
| 5,613,979 A | 3/1997 | Trotta et al. | 606/194 |
| 5,616,114 A | 4/1997 | Thornton et al. | 600/3 |
| 5,617,878 A | 4/1997 | Taheri | 128/898 |
| 5,620,649 A | 4/1997 | Trotta | 264/515 |
| 5,634,936 A | 6/1997 | Linden et al. | 606/213 |
| 5,662,580 A | 9/1997 | Bradshaw et al. | 600/3 |
| 5,662,700 A | 9/1997 | Lazarus | |
| 5,693,088 A | 12/1997 | Lazarus | |
| 5,695,504 A | 12/1997 | Gifford, III et al. | 606/153 |
| 5,702,412 A | 12/1997 | Popov et al. | 606/1 |
| 5,755,775 A | 5/1998 | Trerotola et al. | |
| 5,766,158 A | 6/1998 | Opolski | 604/265 |
| 5,779,731 A | 7/1998 | Leavitt | 606/194 |
| 5,792,095 A | 8/1998 | Kissinger et al. | |
| 5,795,325 A | 8/1998 | Valley et al. | |
| 5,797,879 A * | 8/1998 | DeCampli | 604/93.01 |
| 5,797,934 A | 8/1998 | Rygaard | |
| 5,817,113 A | 10/1998 | Gifford, III et al. | |
| 5,830,222 A | 11/1998 | Makower | 606/1 |
| 5,830,228 A | 11/1998 | Knapp et al. | 606/195 |
| 5,843,027 A | 12/1998 | Stone et al. | 604/53 |
| 5,868,770 A | 2/1999 | Rygaard | |
| 5,893,369 A | 4/1999 | LeMole | |
| 5,925,060 A | 7/1999 | Forber | 606/191 |
| 5,954,706 A | 9/1999 | Sahatjian | |
| 5,961,536 A | 10/1999 | Mickley et al. | |
| 5,976,178 A | 11/1999 | Goldsteen et al. | 623/1 |
| 6,007,576 A | 12/1999 | McClellan | |
| 6,030,392 A | 2/2000 | Dakov | 606/139 |
| 6,042,569 A | 3/2000 | Finch, Jr. et al. | |
| 6,068,637 A | 5/2000 | Popov et al. | 606/159 |
| 6,086,553 A | 7/2000 | Akbik | |
| 6,102,884 A | 8/2000 | Squitieri | |
| 6,113,612 A | 9/2000 | Swanson et al. | |
| 6,171,319 B1 | 1/2001 | Nobles et al. | |
| 6,200,257 B1 | 3/2001 | Winkler | |
| 6,248,117 B1 | 6/2001 | Blatter | |
| 6,254,563 B1 | 7/2001 | Macoviak et al. | |
| 6,261,257 B1 | 7/2001 | Uflacker et al. | |
| 6,264,633 B1 | 7/2001 | Knorig | |
| 6,280,460 B1 | 8/2001 | Bolduc et al. | 606/222 |
| 6,293,965 B1 | 9/2001 | Berg et al. | 623/1.13 |
| 6,319,226 B1 | 11/2001 | Sherry | |
| 6,401,721 B1 | 6/2002 | Maginot | |

OTHER PUBLICATIONS

Apparatus, Hemoperfusion, Sorbent on Neoforma, *the global healthcare marketplace, Gastroenterology/Urology*, located at http://www.neoforma-gu.com/cat-gu/n0o/n0orj6ul.html, 1 pg., printed Dec. 17, 1999.

Xact Medicare Services, Xact Medicare Policy S–107: Hemoperfusion, *Medicare Medical Policy Bulletin, Freedom of Information*, located at http://www.xact.org/policy/s107.html, 1 pg., printed Dec. 17, 1999.

Xact Medicare Services, Xact Medicare Policy S–53: Hemofiltration (Diafiltration) *Medicare Medical Policy Bulletin, Freedom of Information*, located at http://www.xact.org/policy/s107.html, 1 pg., printed Dec. 17, 1999.

Facts about Plasmapheresis, *Plasmapheresis and Autoimmune Disease*, MDA Publications, located at http://www.mdausa.org/publications/fa–plasmaph.html, 4 pgs., printed Dec. 9, 1999.

Publications, *Hemodialysis*, located at http://www.rein.ca/hem–e.htm, 4 pgs., printed Dec. 9, 1999.

*Good Nutrition & Hemodialysis*, located at http://www.nyu.edu/classescompnutrfood/Cecilia%20Fong/index.html 1 pg., printed Dec. 9, 1999.

Tennessee Kidney Clinics and Affiliates, *What is Hemodialysis?* located at http://www.dialysisclinics.com/news2.htm, 1 pg., printed Dec. 9, 1999.

*Good Nutrition & Hemodialysis*, located at http://www.nyu.edu/classes/computrfood/Cecilia%20Fong/index.html, 1 pg., printed Dec. 9, 1999.

Mulzer, S.R. and Brash, J.L., *Identification of Plasma Proteins Adsorbed to Hemodialyzers During Clinical Use*, Journal of Biomedical Materials Research, vol. 23, 1483–1504 (1989).

Ljungberg, B., et al., *Effective Anticoagulation by a Low Molecular Weight Heparin (Fragmin®) in Hemodialysis with a Highly Permeable Polysulfone Membrane*, Clinical Nephrology, vol. 38, No. 2–1992 (97–100).

Jen Ming Yang, et al., *Preparation of Heparin Containing SBS–g–VP Copolymer Membrane for Biomaterial Usage*, Journal of Membrane Science 138 (1998) 19–27.

Brittinger, Wolf Dieter et al., *Vascular Access for Hemodialysis in Children*, Pediatric Nephrology, 1997, pp. 11:87–95.

* cited by examiner

VASCULAR OCCLUSAL BALLOONS AND RELATED VASCULAR ACCESS DEVICES AND SYSTEMS

RELATED APPLICATIONS

This application is a continuation-in-part patent application of U.S. patent application Ser. No. 09/480,964 entitled Vascular Access Devices and Systems which was filed on Jan. 11, 2000 on behalf of Duane D. Blatter. This application is also a continuation-in-part patent application of U.S. patent application Ser. No. 09/481,283 entitled Methods for External Treatment of Blood which was filed on Jan. 11, 2000 on behalf of Duane D. Blatter. Ser. No. 09/480,964 and Ser. No. 09/481,283 are both incorporated herein by specific reference.

BACKGROUND OF THE INVENTION

1. The Field of the Invention

The present invention relates to vascular access systems and devices. In particular, the present invention relates to vascular access systems and devices, that permit access to the blood flow while avoiding repeated punctures into the blood vessel being accessed.

2. Present State of the Art

Procedures that require the repeated access to blood vessels include dialysis and the delivery of medicines for an extended period of time. The multiple punctures that such repeated access necessitates eventually render the blood vessel unsuitable for further effective injections. In addition, some external blood treatment methods rely on the extraction of blood from an artery and on the subsequent injection of the treated blood into a vein. The characteristics of the fluid flow in an artery are significantly different from the characteristics in the fluid flow in a vein. These fluid flow dissimilarities may lead to additional adverse effects that detrimentally affect the long term accessibility of the blood vessels that must be accessed for the external blood treatment to be effectively performed. For example, in an arterio-venous graft constructed as a vascular access for dialysis, the blood flow and blood pressure characteristic of the arterial circulation are so different from the blood flow and blood pressure in the vein into which the blood of the AV graft flows, that the vein usually develops hyperplasia and stenoses.

It is desirable to provide devices, systems and methods that permit multiple access to a blood vessel for the purpose of delivering medicines into the patient's blood stream in such a way that the receiving blood vessel is not so severely damaged that it becomes unavailable after a few medicine administrations.

It is also desirable to provide devices, systems and methods that permit multiple access to a blood vessel for external blood treatment, such as hemodialysis, in such a way that the blood vessel being accessed does not become unavailable for successive dialysis operations.

Furthermore, it would be desirable to provide a device that is suitable for multiple vascular access for the purpose of long term medicine delivery into the patient's blood flow and also for the purpose of effectively practicing hemodialysis for a long period of time.

The practical advantages of such devices and systems would be considerably enhanced if the device or system is lodged subcutaneously and is reliably attachable to a blood vessel by anastomosis techniques. In addition, such a vascular access device or system would have to be appropriately configured to allow for controlled and selected blood flow through the device or system and to allow for a controlled delivery of physiologically active agents, such as medicines. These goals should be accomplished while minimizing, or avoiding to the maximum extent possible, undesirable adverse effects such as vessel thrombosis, blood stagnation, the formation of undesirable turbulence, and the formation of blood clots.

The present invention focuses on objectives described hereinbelow for solving problems which are associated with repeated vascular access, and provides devices, systems and methods with advantageous features for solving such problems.

OBJECTS AND BRIEF SUMMARY OF THE INVENTION

A blood vessel that is repeatedly accessed, and in particular repeatedly punctured, deteriorates to the point that vascular access becomes increasingly difficult and eventually impossible. When vascular access places the blood vessel under exceptional fluid dynamics conditions or subjects the vascular tissues to the deleterious side effects of certain medications, vascular deterioration can be seriously accelerated. An example of such exceptional fluid dynamics conditions is the blood volume and pressure that a vein is subjected to when it receives the arterial blood flow from an AV (arterio-venous) graft that has been created to provide vascular access for dialysis.

Although an occasional vascular access can be performed at any one among a plurality of generally available access sites, the availability of vascular access sites for the intravenous delivery of medicine for a long period of time or for dialysis can be seriously diminished because vascular access under such conditions has to be performed repeatedly. For example, hemodialysis typically requires from about 150 to about 200 vascular access operations per year for a period that typically ranges form about 2 years to about 5 years.

It is therefore desirable to provide vascular access devices and systems that can be repeatedly accessed, and in particular repeatedly punctured, while avoiding the deleterious effects on the blood vessel itself. These systems and devices should be biocompatible and in particular they should not significantly perturb the normal blood flow within the blood vessel that is to be accessed. In addition, these systems and devices should be made of readily available materials that can be clinically manipulated according to known techniques. It is also desirable to provide methods for repeatedly accessing blood vessels, and in particular for repeatedly accessing veins in the practice of vein-to-vein hemodialysis, so that vein accessibility is not diminished by the repeated vein access.

The general object of this invention is to provide vascular access systems and devices that facilitate repeated vascular access while reducing, or even eliminating, the deleterious effects that the vascular tissue would otherwise be subjected to. More specifically, it is an object of this invention to provide vascular access systems and devices that permit access to the blood stream while avoiding repeated punctures into the blood vessel being accessed.

It is another object of this invention to provide vascular access systems and devices that can be attached to a blood vessel by known anastomosis techniques.

It is another object of this invention to provide vascular access systems and devices that can be used for the intravenous long term delivery of medicines and also be used in dialysis.

It is a further object of this invention to provide methods for external treatment of blood such as hemodialysis methods, and in particular vein-to-vein hemodialysis methods, that enable the practice of hemodialysis between two blood vessels, such as two veins, while avoiding deleterious effects on these vessels. These deleterious effects would otherwise reduce blood vessel accessibility thus rendering the number of feasible hemodialysis operations unacceptably small.

These and other objects of this invention are preferably achieved by devices that come an occlusal balloon in fluid communication with a port device, and by systems that comprise an occlusal balloon in fluid communication with a port device to be used in conjunction with a graft vessel that in turn is configured to be anastomosed to a blood vessel.

The devices and systems of this invention preferably feature materials that are suitable for their subcutaneous disposition. This feature advantageously permits the placement of the vascular access systems and devices at a location that is not directly exposed to external pathogens.

The devices and systems of this invention preferably feature materials that can be repeatedly punctured and that are self-sealing. These features advantageously permit multiple injection to and extraction from the vascular access systems and devices of a variety of fluids such as blood samples, biocompatible solutions, medicines, and blood to be dialyzed or to be received from a dialysis apparatus.

The devices and systems of this invention preferably incorporate features that facilitate the exposure of the blood stream to desired physiologically effective (or bioactive) agents. This exposure is achieved by contact or by transport phenomena. In any case, these features advantageously permit, inter alia, the delivery into the blood stream of medications at desired and controlled dosages. Another advantage derived from these features is that the blood stream can be exposed to an agent that prevents the formation of blood clots.

In one embodiment, an occlusal balloon is positioned in a graft vessel and is in fluid communication with a port device. The occlusal balloon may be impermeable or it may have permeable portion such as an integral permeable region or a permeable membrane attached to its delivery end. In an another embodiment the occlusal balloon and the graft vessel are integral.

Selective and controlled exposure to a physiologically active agent, such as heparin, is in some preferred embodiments, provided by letting such agent migrate from the interior of an occlusal balloon into the blood in the vessel being accessed. This migration of a physiologically active agent is preferably realized by diffusion across a semipermeable region or membrane of adequately chosen porosity. In addition, preferred embodiments of the semipermeable region or membrane function according to the present invention by allowing the migration of an aqueous fluid from the blood stream in the vessel being accessed into the interior of an occlusal balloon. This migration of aqueous fluid is preferably realized by permeation across a semipermeable region or membrane of adequately chosen porosity. By migrating from the blood stream into the interior of an embodiment of an occlusal balloon, this aqueous fluid keeps the occlusal balloon in a distended configuration by osmosis, thus preventing the invasion of the anastomosed graft by blood from the accessed vessel.

The methods of this invention focus on repeated vascular access that is facilitated by preferably subcutaneous devices and systems which can be repeatedly punctured while preserving their physical integrity, biocompatibility and operability. These characteristics advantageously permit the practice of hemodialysis according to the methods of this invention for the extended periods of time that are typically needed by patients.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to vascular access systems and devices, and in particular to venous access systems and devices, that permit access to the blood flow while avoiding repeated punctures into the blood vessel being accessed. To this end, an exemplary embodiment of the system of the present invention includes the following components: a graft vessel that is adapted for being anastomosed to the blood vessel that is to be repeatedly accessed, an occlusal balloon, a port device, and a semipermeable membrane that permits the selective and controlled exposure of the blood flow to an agent such as a physiologically active agent.

Figure 7A:
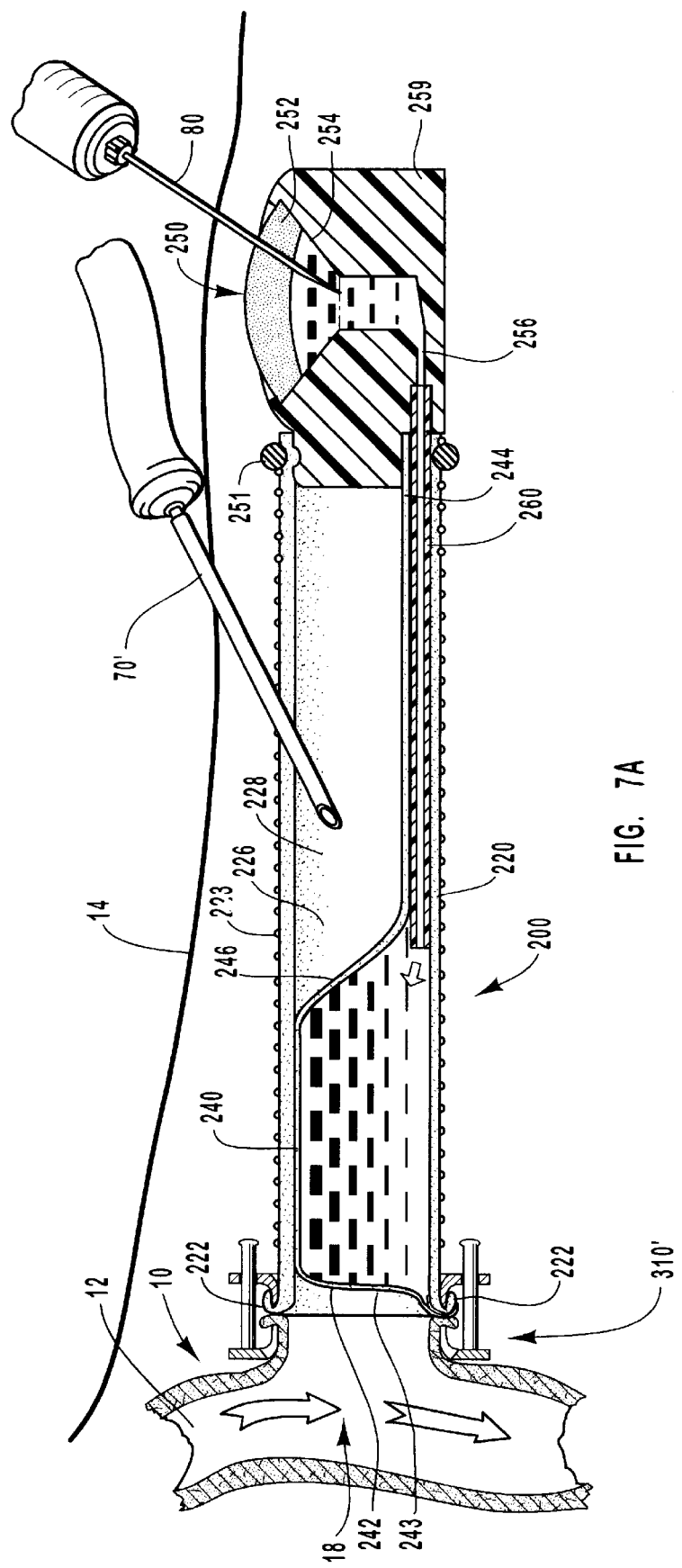
FIG. 7A is a partial cross sectional view of an embodiment of a vascular access system with an occlusal balloon that extends integrally from the graft vessel. The graft vessel of the system is attached to the blood vessel by a compression plate assembly and the occlusal balloon has been filled.
Figure 7B:
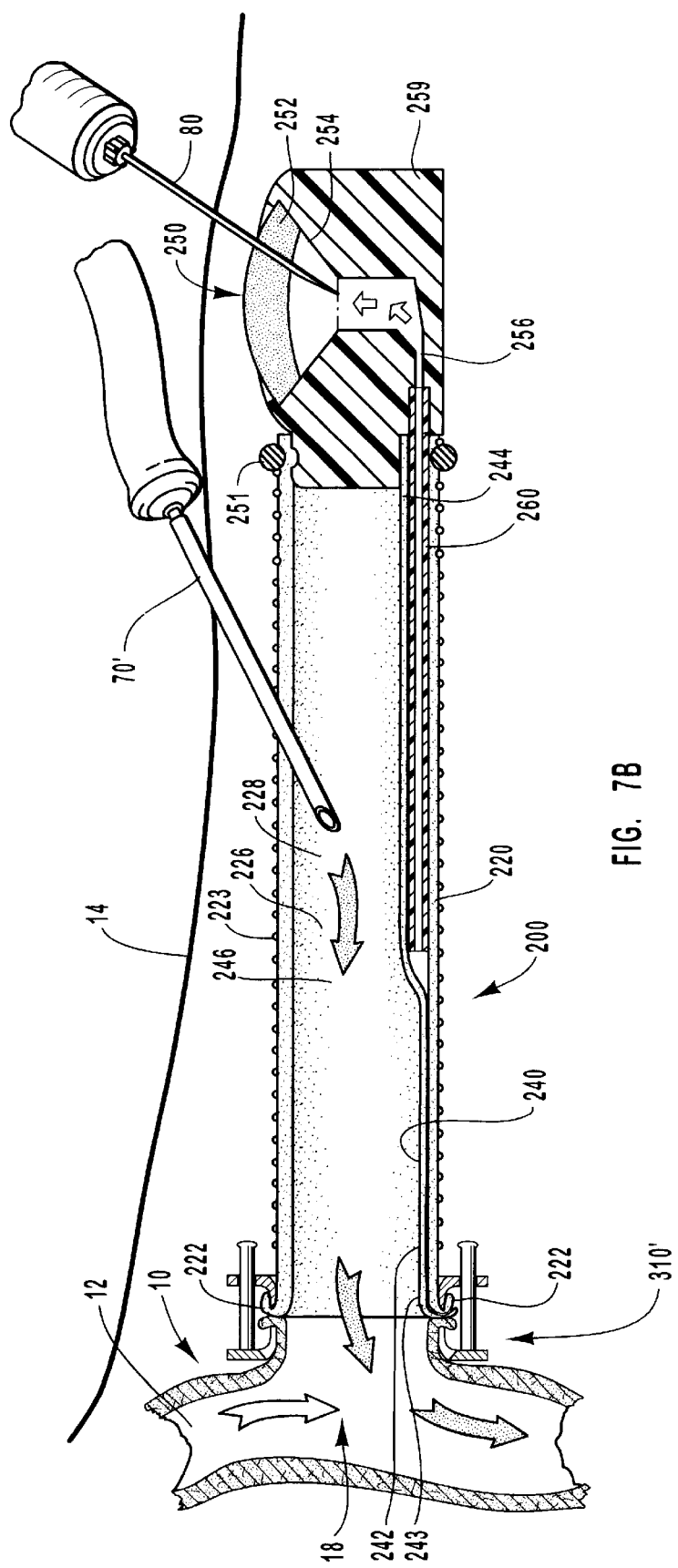
FIG. 7B is a partial cross sectional view of the embodiment shown in FIG. 7A with the occlusal balloon deflated.

Several different embodiments of the occlusal balloon are disclosed herein. These embodiments are respectively shown at 40 in FIG. 1A, at 40' in FIGS. 2A–2B, at 40" in FIG. 3, at 40a and 40b in FIG. 4, and at 140 in FIGS. 7A–7B. Occlusal balloon 40 may be an impermeable balloon or it may have a permeable or semipermeable region at its delivery end 42. The benefits of a permeable or semipermeable region are discussed in detail below. Occlusal balloon 40' has a membrane 43' at its delivery end 42' that is preferably semipermeable. Occlusal balloon 40" has a semipermeable membrane 43" that is laminated to the delivery end 42". Occlusal balloons 40a and 40b shown in FIG. 4 have separate membranes 43a and 43b. Occlusal balloon 140 shown in FIGS. 7A–7B is integral with graft vessel 120. Each of these embodiments is discussed in detail below. These balloons are all part of devices or systems such as those identified at 100, 100', 100", 200.

A common feature of these balloons is that they are adapted for distension and contraction within a graft vessel at an anastomosis site after the graft vessel has been anastomosed to a blood vessel. When expanded in a distended position the balloon blocks fluid communication between the graft vessel and the blood vessel as shown in FIGS. 1A, 2A, 3, 6 and 7A. When deflated to a contracted position, the balloon permits fluid communication between the graft vessel and the blood vessel as shown in FIGS. 2B and 7B. The benefit of this arrangement is that the graft vessel can be repeatedly punctured to provide access for blood treatments. This provides a significant improvement over conventional techniques that require repeated puncturing of a blood vessel.

Figure 1A:
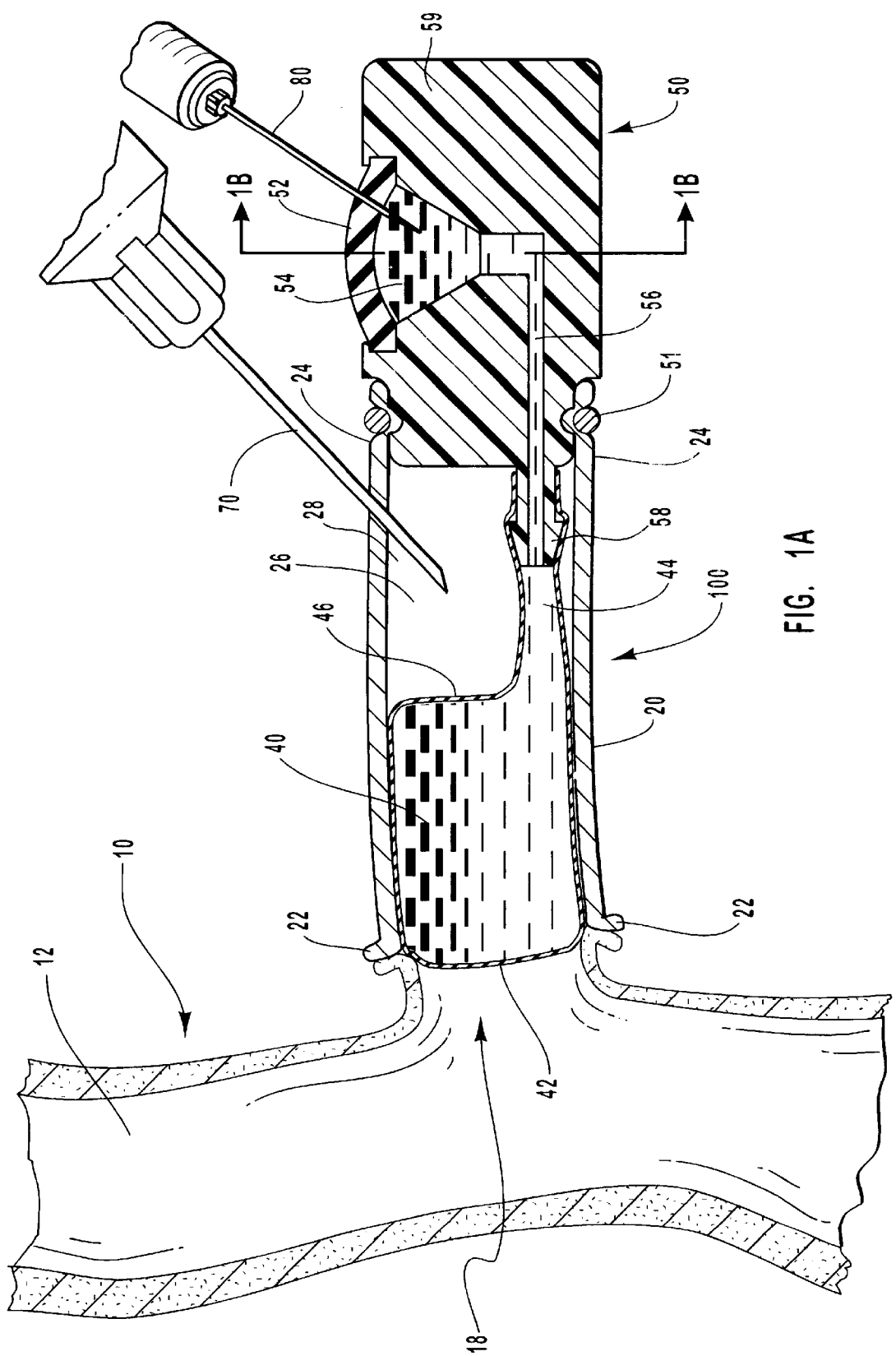
FIG. 1A is a partial cross sectional view of an embodiment of a vascular access system with an occlusal balloon.
Figure 1B:
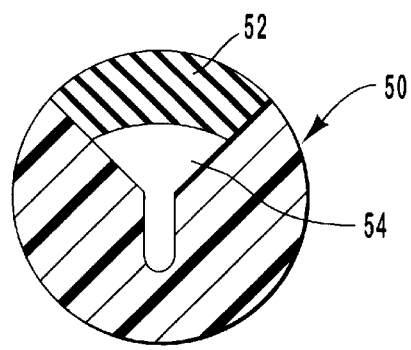
FIG. 1B is a partial cross sectional view of the port device of the embodiment shown in FIG. 1A.

FIG. 1A schematically and generally shows in a cross sectional view relevant features of this invention as illustrated by an exemplary embodiment. Blood vessel 10 in this exemplary embodiment is accessed with the aid of a graft vessel 20 that is anastomosed to a blood vessel 10 at an anastomosis site 18 by any suitable methodology. Graft vessel 20 houses, in this particular embodiment, occlusal balloon 40 with a delivery end 42 and an access conduit or end 44.

Graft vessel 20 is shown in FIG. 1A after its anastomosis end 22 has been anastomosed to blood vessel 10 at anastomosis site 21. As illustrated by the embodiment shown in FIG. 1A, delivery end 42 of occlusal balloon 40 generally corresponds with anastomosis end 22 of graft vessel 20 in the sense that both ends are generally located in the region of the anastomosis site 21.

Once graft vessel 20 has been anastomosed to blood vessel 10, then graft vessel 20 remains subcutaneously located along with a port device 50 which is attached to port end 24 of graft vessel 20 opposite from anastomosis end 22. This arrangement enables a hypodermic needle 70 or a similar medical device to be inserted from outside of the patient's body, as indicated by body surface 14, and to then inject or draw fluids into lumen 26 of graft vessel 20 once balloon 40 has been deflated. This arrangement also enables a hypodermic needle 70 to flush lumen 26 by repeatedly injecting and drawing fluids draw fluids from the lumen 26 of graft vessel after balloon 40 has been sufficiently inflated to occlude graft vessel 20. Note that graft vessel 20 is made of a material such as polytetrafluoroethylene (PTFE) or some other biocompatible self sealing material that can be repeatedly punctured and that is preferably self sealing.

Port device 50 provides access to balloon 40 and enables a hypodermic needle 80 to inject fluids into balloon 40 and to draw fluids from balloon 40. The exemplary embodiment of port device 50 shown in FIG. 1A is also shown in a schematic cross-sectional view along plane 1B—1B in FIG. 1A. Elements in the cross sectional view are labelled with the same numbers as the corresponding elements are labelled in FIG. 1A.

Port device 50 has a self-sealing cover 52 that is adapted to receive a hypodermic needle 80 or any other medical instrument that is typically used to inject fluid into or to draw fluid from a cavity. Embodiments of the self-sealing cover according to this invention are preferably made of silicone rubber. Port device 50 preferably has a chamber 54 that is in fluid communication with a conduit 56. Chamber 54 is preferably funnel shaped as shown in order to guide the needle 80. Conduit 56 is preferably oriented perpendicularly relative to funnel shaped chamber 54. Conduit 56 extends through a coupler 58 and is in fluid communication with occlusal balloon 40. Balloon 40 is coupled to port device 50 by inserting coupler 58 into access end 44 of balloon 40. Coupler 58 may be flared as shown and access end 44 is sized to ensure a secure frictional engagement. Port device 50 is preferably located in housing 59.

As shown in the example depicted in FIG. 1A, port end 24 of graft vessel 20 is detachably connected to port device 50 by a pressure device 51 that exerts sufficient pressure to maintain the leak proof attachment of graft vessel 20 to port device 50. Pressure device 51 can in particular be embodied by an O-ring or by any other device that exerts sufficient pressure to maintain the leak proof attachment of graft vessel 20 to port device 50. This leak proof attachment can be accomplished in other embodiments of this invention by a threaded engagement, a snap joint engagement, a bound engagement, an adhesive bound engagement, combinations of these features or by any type of leak proof engagement that is well known in the art. Embodiments of the port device are preferably made of stainless steel or titanium, although other biocompatible materials can also be used, particularly other biocompatible materials that are preferably resistant to the abrasion of sharp needle tips.

Figure 1C:
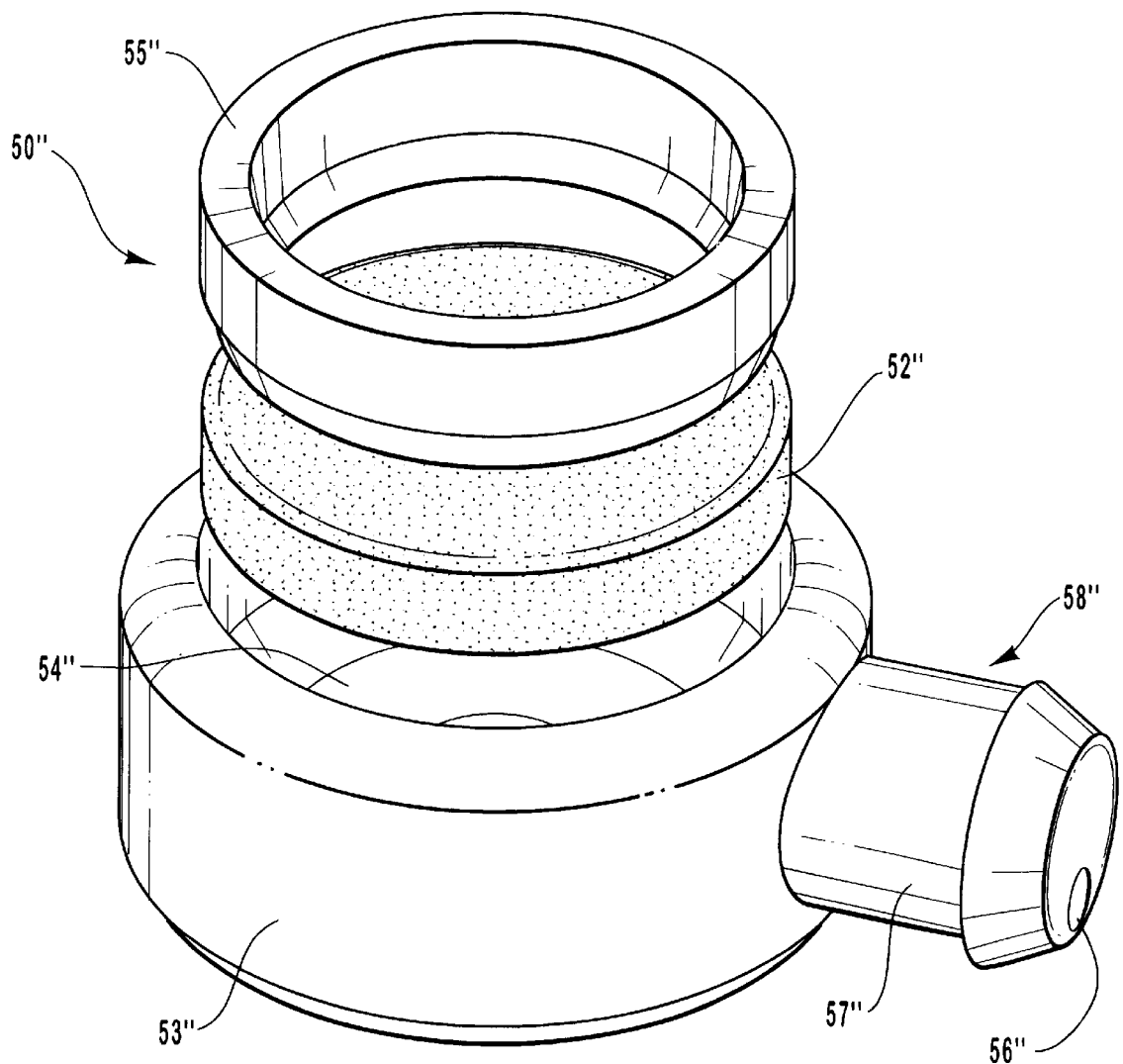
FIG. 1C shows a perspective view of an embodiment of a port device.

Port devices such as port device 50 are common medical devices. Commercially available port devices for vascular access include devices that are marketed by Horizon Medical Products of Atlanta, Ga., under the trademarks OmegaPort®, TitanPort®, and Vortex®; by SIMS Deltec, Inc. of Saint Paul, Minn. under the trademarks P.A.S. Port® and P.A.S. Port® II and also by Smiths Industries Medical Systems. FIG. 1C depicts another embodiment of a port device 50' in an exploded perspective view. Port device 50' has a body 53', a self sealing cover or plug 52' and a compression ring 55'. Ring 55' is an example of means for keeping self sealing cover 52' within body 53' to effectively seal funnel shaped chamber 54'. Body 53' is provided with a coupler 58' to establish leak proof fluid communication between chamber 54' and the interior of an occlusal balloon. A conduit 56' establishes fluid communication between chamber 54' and the interior of an occlusal balloon attached to coupler 58'.

As indicated above, occlusal balloon 40 can be inflated with a fluid provided thereto through port device 50, in which case occlusal balloon 40 prevents the flow of blood into graft vessel 20 by occluding and effectively sealing anastomosis site 21. As also indicated above, occlusal balloon 40 can be selectively deflated by drawing its fluid content through port device 50, in which case blood flow from blood vessel 10 invades the interior of graft vessel 20 through anastomosis site 21. Embodiments of inflatable balloons according to the present invention, are made of any elastic biocompatible material, such as rubber, PTFE particularly expanded PTFE (ePTFE), latex, polyurethane, polyethylene teraphthalate (PET), silicone and combinations of these materials. When the embodiment of the inflatable balloon comprises a membrane that is attached to the balloon with an adhesive, the balloon material is preferably gluable, such as silicone rubber.

When blood flow from blood vessel 10 reaches the interior of graft vessel 20 because occlusal balloon 40 is in a deflated configuration, graft vessel 20 can be punctured by a needle to perform a procedure, for example a hemodialysis, or to deliver a medication. When the dialysis session is finished, occlusal balloon 40 can be inflated again by injecting an appropriate fluid through port device 50 via needle 80 and any remaining blood left in lumen 26 can be drawn out of this space and replaced with a fluid such as saline solution or any other appropriate biocompatible fluid.

Note that balloon 40 is preferably shaped when distended in its inflated configuration such that it does not entirely fill lumen 26. More particularly, balloon 40 has a chamber portion 46 that defines a chamber 28 within lumen 26 along with access conduit or end 44, port device 50 and graft vessel 20. As shown in FIG. 1A, needle 70 may be inserted into chamber 28 for repeated flushing of chamber 28 after balloon 40 has been reinflated upon the completion of a procedure. Embodiments of this invention that are provided with an occlusal balloon are preferably configured in a way such that the access end of the occlusal balloon and the port device are separated by several centimeters so that there is a chamber 28 within lumen 26. In some embodiments, however, the inflated occlusal balloon can extend up to and be in contact with the port device.

In its inflated configuration as shown in FIG. 1A, occlusal balloon 40 is filled with a fluid that causes, or in some embodiments contributorily causes, the expansion within elastic compliance limits of such a balloon to effectively seal the graft vessel at the anastomosis site. A preferred embodiment of this invention comprises an occlusal balloon which can be repeatedly inflated and deflated within its elastic compliance limits.

Balloon 40 may be an impermeable occlusal balloon that is injected with a fluid that directly causes the inflation of the occlusal balloon. Since the fluid cannot diffuse out of the occlusal balloon, the balloon is inflated or deflated by removal of the fluid through port device 50. The fluid may be any suitable liquid or gas.

Blood flow stagnation in the region near anastomosis site 18 should be minimized and preferably avoided. To this end, occlusal balloon 40 is so configured as to be able to seal the anastomosis site in a way such that no significant cavity is formed at anastomosis site 18. The presence of a cavity or substantially recessed space in this region may lead to blood flow stagnation or to a clot. In addition, a cavity or substantially recessed space can lead to the formation of unacceptably turbulent blood flow when the device is anastomosed to an artery.

A plurality of factors may cause blood flowing in lumen 12 of blood vessel 10 to coagulate in the region near anastomosis site 18 resulting in vessel thrombosis. These factors include the presence of foreign bodies used in the anastomosis procedure, irregularities at anastomosis site 18, and disrupted intima at anastomosis site 18. To prevent this formation of blood clots, blood flowing in lumen 12 is exposed in the region near to delivery end 42 to an anticoagulant agent that is provided with the aid of uniquely adapted occlusal balloons as described below in detail.

Figure 2A:
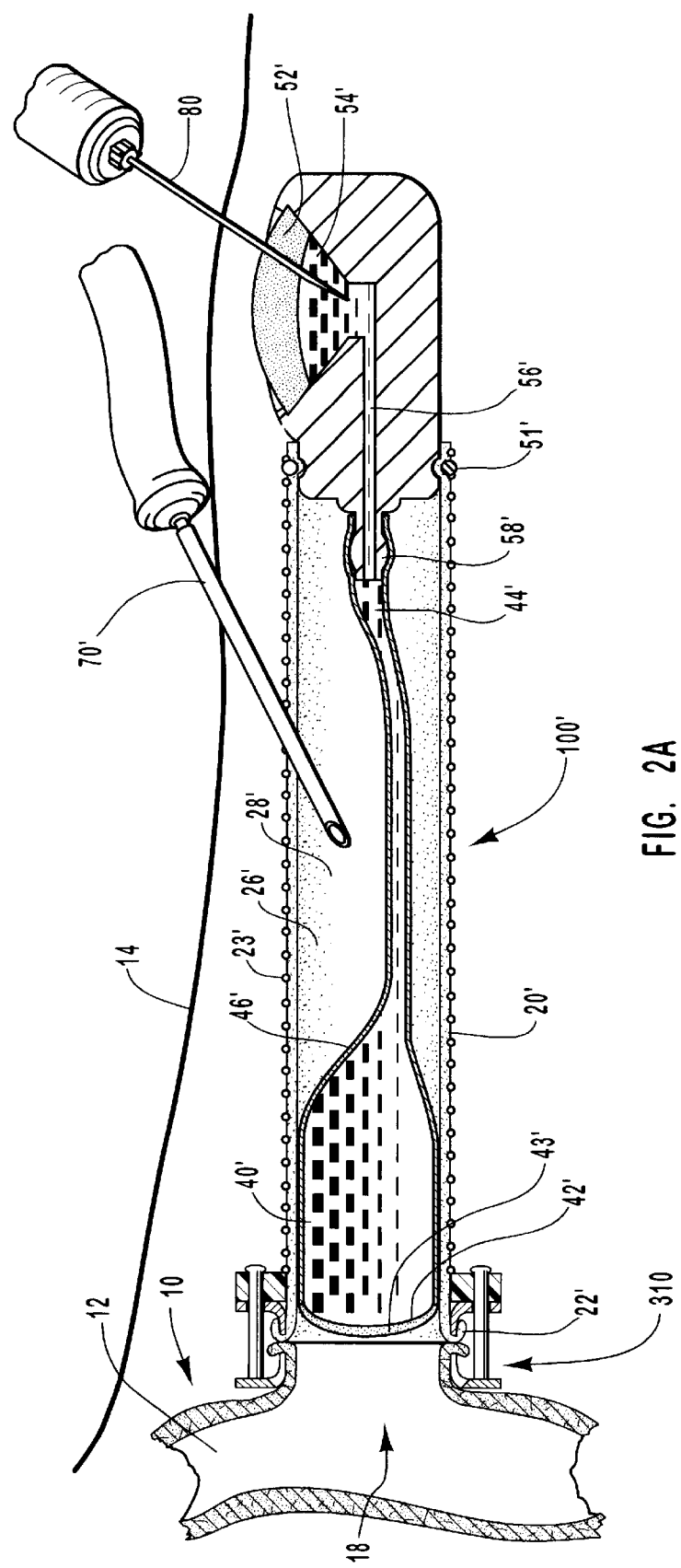
FIG. 2A is a partial cross sectional view of an occlusal balloon in a graft vessel that is coupled to a port device. The occlusal balloon has a semipermeable membrane at its delivery end and is coupled to a port device at its other end. The occlusal balloon is inflated.
Figure 2B:
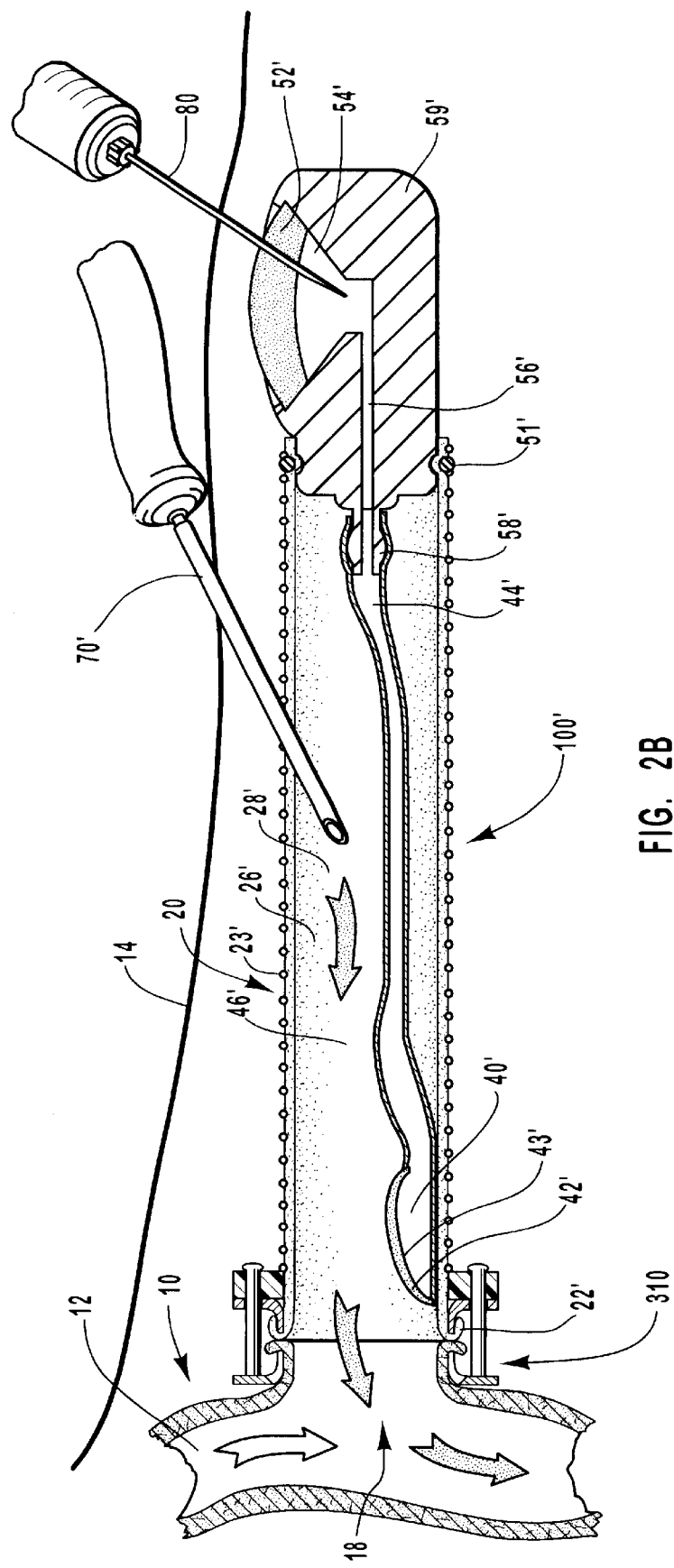
FIG. 2B is a partial cross sectional view of the system shown in FIG. 2A with the occlusal balloon deflated.

While balloon 40 may be impermeable so that the fluid used to inflate and deflate the balloon remains in the balloon, balloon 40 may also have a permeable or semipermeable region at its delivery end 42. A balloon having such a semipermeable or permeable region at its delivery end allows for fluid transport out of and into the interior of the occlusal balloon. As shown in FIGS. 2A–2B, a balloon 40' may also have a delivery end 42' with a membrane 43' that is permeable or semipermeable. Such regions and membranes are examples of semipermeable portions of a balloon that enable the balloon to deliver an anticoagulant locally to the anastomosis site 18. Additionally, a balloon having a semipermeable region, may be initially inflated by a fluid injected into the occlusal balloon; however, other phenomena, such as osmosis, cause the occlusal balloon to remain in an inflated configuration, as described below.

A balloon having a semipermeable membrane 43' and a balloon having an integral semipermeable region such as balloon 40 may both be utilized to deliver an anticoagulant agent or another physiologically active agent. More particularly, such semipermeable balloons are designed with an integral semipermeable region or a semipermeable membrane that has a selective porosity. After a fluid is delivered into the interior of the occlusal balloon that contains a physiologically active agent, particularly anticoagulants such as heparin at the appropriate dosage, then the porosity of the semipermeable region or membrane permits the anticoagulant, such as heparin, to pass out of the balloon be transported into luminal space 12 of blood vessel 10 at the anastomosis site 18. These features and elements of a vascular access device according to this invention function to provide a selective and controlled exposure, and more specifically, to provide a selective and controlled transport.

The porosity is also preferably selected to permit aqueous fluid from the blood stream in blood vessel 10 to migrate through the semipermeable region or semipermeable membrane of the balloon and into the balloon to keep the occlusal balloon in a distended configuration by osmosis. So by properly designing the semipermeable region or membrane, osmotic pressure is utilized to permit the flow of aqueous fluid from the blood flow in blood vessel 10 into the interior space of occlusal balloon 40. Osmosis can be accomplished by delivering into the interior of occlusal balloon 40 a fluid that contains a preferably biocompatible substance that cannot permeate across the membrane through which heparin or another physiologically active agent is delivered. An example of such substance is albumin. The fluid within occlusal balloon 40 thus contributes in providing the adequate conditions for osmosis to take place and hence to the maintenance of occlusal balloon 40 in an inflated configuration as heparin, or some other substance, diffuses from the interior of occlusal balloon 40 into the blood flow in blood vessel 10.

In addition to, or instead of, heparin or another anticoagulant, an occlusal balloon having a permeable or semipermeable delivery end such as 40 and 40' can be used to deliver a medication, and in particular a medication for a long term treatment of a chronic disease. This medication can also be delivered by letting it diffuse across a permeable region at delivery end 42 of occlusal balloon 40 or through a permeable membrane 43' of occlusal balloon 40'. In the exemplary embodiment shown in FIG. 1A, heparin and any other substance that diffuses through a semipermeable membrane at delivery end 42 can be periodically supplied to the interior space of occlusal balloon 40 by injection through port device 50. Similarly, port device 50' can be utilized to resupply balloon 40'.

In the practice of hemodialysis and also in the prolonged delivery of medicine for the treatment of a chronic disease, the occlusal balloon of this invention typically contains an aqueous solution that includes a high molecular weight substance that cannot diffuse through the pores of the chosen semipermeable region or membrane and at least one physiologically active agent of a smaller molecular weight that can diffuse through the pores of the chosen semipermeable region or membrane. As indicated above, the preferred high molecular weight substance is albumin and the preferred physiologically active agent is typically heparin.

In some of the embodiments of this invention, heparin is the physiologically active agent and also the solute whose concentration gradient gives rise to the osmotic pressure that keeps the occlusal balloon inflated. The occlusal balloon holds in these embodiments a relatively large volume of solution so that the concentration of heparin does not decrease too rapidly as a consequence of its diffusion rate across the properly chosen semipermeable region or membrane.

The aqueous solution of albumin and heparin provides the concentration gradient driving the osmotic process which in turn keeps the occlusal balloon in an inflated configuration. Osmosis in this context involves the diffusion of aqueous fluid from the blood in the blood vessel being accessed into the interior of the occlusal balloon through the pores of an appropriately selected semipermeable region or membrane that is in contact with the blood flow at the anastomosis site. Albumin used in this invention is preferably human albumin with a molecular weight of approximately 65000.

Heparin diffuses through the pores of such semipermeable membrane into the blood in the blood vessel which is being accessed, thus preventing the coagulation of blood that might otherwise take place as a consequence of a variety of factors that are associated with the features of the anastomosed structures. The molecular weight of the heparin preferably used in embodiments of the present invention ranges from about 500 to about 18000. Heparin inhibits reactions that lead to the clotting of blood and the formation of fibrin clots both in vitro and in vivo. The clinical pharmacology of heparin is that of a substance that acts at multiple sites in the normal coagulation system. In particular, small amounts of heparin in combination with antithrombin III (heparin cofactor) can inhibit thrombosis by inactivating activated Factor X and inhibiting the conversion of prothrombin to thrombin. Once active thrombosis has developed, larger amounts of heparin can inhibit further coagulation by inactivating thrombin and preventing the conversion of fibrinogen to fibrin. It is reported that heparin also prevents the formation of a stable fibrin clot by inhibiting the activation of the fibrin stabilizing factor.

In choosing the appropriate concentrations of albumin and heparin, however, a variety of determining factors have to be taken into consideration. Heparin and albumin associate to some extent. This association leads to the effective sequestering of heparin that is not available to diffuse into the blood stream. In addition, some of the albumin can be adsorbed on the semipermeable region or membrane, thus decreasing the effective concentration of albumin that influences osmosis.

The concentration of albumin is accordingly determined so that the osmotic pressure is comparable to and slightly greater than the vascular pressure in the blood vessel being accessed. For example, venous pressure is typically in the approximate range of about 5 mmHg to about 15 mmHg, and rarely exceeds 30 mmHg, in which case a venous vascular access according to this invention should preferably provide an albumin solution in the occlusal balloon at an osmotic pressure slightly greater than 30 mmHg, such as in the approximate range of about 35 mmHg to about 45 mmHg.

"Nominal molecular weight pore size portion" including an integral region or an attached membrane in this context characterizes a semipermeable region or membrane whose pore size is such that particles whose molecular weight is less than the given nominal molecular weight are able to diffuse through the pores of the semipermeable region or membrane, whereas substances whose molecular weight is greater than or about equal to the given nominal molecular weight cannot diffuse through the pores. Unless otherwise indicated, molecular weights given herein are expressed in Daltons; albumin concentration units given herein are expressed as a percentage that refers to mass in grams of albumin in 100 ml of solution, and heparin concentration units are expressed as International Units (IU) heparin per ml of solution.

Any material having a molecular weight that is greater than or about equal to the given nominal molecular weight of materials that can diffuse through the pores can be utilized as a nontransportable material or as an osmotic agent. In addition to albumin, another example of such a nontransportable material that has a can be utilized to fill the occlusal balloon is a gel. The gel is preferably a water soluble gel. The gel is preferably salt free or at least substantially free of salts. An example of a suitable water soluble gel that is substantially free of salts is the gel sold as AQUASONIC® 100 gel by PARKER LABORATORIES, INC. Another suitable commercially available gel is SURGILUBE® 100 gel sold by E. Fougera & Co. Other examples of water soluble gel materials that can be utilized with water to form a water soluble gel include carboxypolymethylene, polyacrylic copolymers, gums, polyethylene oxides, proteins, and mixtures thereof. As indicated above, the water soluble gel is preferably salt free in order to provide an appropriate osmotic gradient.

An advantage of gels such as the gel sold as AQUASONIC® 100 gel is that the molecules are larger than albumin which enables their use with balloons having a different range of porosity. More particularly, the pores or passageways in some types of PTFE are too large to retain albumin so gels may be more appropriately utilized. Balloons formed from PET may have pores or passages that are small enough that albumin can be used, however, gels are preferred.

The ratio of heparin to osmotic agent depends on the type of osmotic agent such as gel or albumin. For example, the ratio of heparin to the osmotic agent may range from about 1:1 to about 10:1. However, a preferred ratio is about 4:1 for the volume of heparin to the volume of a water soluble gel such as the gel sold as AQUASONIC® 100 gel. Note that the preferred ratio depends on the porosity of the permeable region or membrane of the balloon. Note also that decreasing the heparin concentration decreases the antithrombogenic effect while increasing the heparin concentration increases the osmotic gradient.

Note that an impermeable membrane such as balloon 40 that does not have a permeable region may be filled with any suitable material. For example, any gel material described above can be utilized as well as albumin.

Membranes such as membrane 43' are preferably formed from polyethersulfone and are most preferably the semipermeable material sold as Biomax® membranes from the Millipore Corp. or Bedford, Mass. This semipermeable membrane is available in several nominal molecular weight pore sizes in the range from about 5000 to about 50000. Preferred membranes for embodiments of this invention are characterized by a pore size in the range from about 30000 to about 50000 nominal molecular weight. Among these types of semipermeable membrane, a more preferred type is a membrane with a nominal molecular weight pore size of about 50000.

In general, preferred membranes for embodiments of this invention are ultrafiltration membrane materials. In addition to the Biomax® membrane, Millipore provides other membranes such as regenerated cellulose membranes sold as Amicon™ 4M membranes which have a nominal molecular weight pore size of about 1000 to about 100000, and hydrophilic polysulfone membranes sold as Amicon™ Zm membranes which have a nominal molecular weight pore size of about 500 to about 500000.

Generally, semipermeable membrane base materials include polymeric materials such as polytetrafluoroethylene, polysulfone, polyamide, polyacrylonitrile, and cuprophane of the adequate pore size, although the hydrophobicity of some polymers requires the treatment of the base material prior to its use as a semipermeable membrane.

Clinical dialyzer materials that can be used in the context of this invention include a cuprophane material sold as CF 15.11 from Baxter Health Care Corp., Deerfield, Ill.; cellulose acetate material sold as COAK 4000 and saponified cellulose ester sold as SCE from Cordis Corporation of Miami, Fla.; polymethylmethacrylate Filtryzer membranes from Toray Industries of Tokyo, Japan; cuprammonium material sold as Rayon from Terumo Corporation of Tokyo, Japan; and cuprophane material sold as Hemoflow D3 and polysulfone material sold as Hemoflow 60 from Fresenius A.G., Germany.

The polyethersulfone membrane used in embodiments of this invention are preferably conditioned prior to its use by immersing it in an albumin solution. For example, by immersing it in a 10% albumin aqueous solution for about one week. Once conditioned, the membrane can be repeatedly used as long as it is not allowed to substantially dehydrate.

When the balloon has an integral semipermeable region such as balloon 40, then the balloon may be formed from a single material that is treated to be impermeable with the exception of the region at delivery end 42 that is intended to be permeable or semipermeable. For example, the balloon may be formed from expanded PTFE that is then soaked or coated with a solution that fills the pores or passageways of the PTFE. The solution may, for example, comprise polyurethane, such as TecoFlex® polyurethane from Thermedics, Inc., soaked in tetrahydrofuran. The solution fills the pores and then the tetrahydrofuran evaporates leaving the polyurethane.

The balloon may also be integrally formed from polyethylene terephthalate (PET) with a semipermeable region at its delivery end. A source of PET that is appropriate for some embodiments is sold by Advanced Polymers of New Hampshire. The semipermeable region of the balloon formed from PET may, for example, be formed by bombarding the region that is desired to be semipermeable, with high energy particles from a linear accelerator and then contacting the region with a solvent to further enlarge the holes made by the high energy particles. Such a process is disclosed by Mark A. Saab in the article entitled "Applications of High-Pressure Balloons in the Medical Device Industry" in Medical Device and Diagnostic Industry, September 2000, at pages 86–97.

As indicated above, although preferred embodiments of occlusal balloons according to this invention include a semipermeable region or membrane that allows for transport and is part of the osmosis that keeps the occlusal balloon inflated, other embodiments of the occlusal balloon do not include a semipermeable region or membrane. For example, some embodiments of the occlusal balloon are inflated by the injection of a fluid that is kept within the balloon while it is inflated, with no osmosis contributing to its distension. These embodiments of impermeable occlusal balloons may be configured so that the exposure to a physiologically active agent of the blood in the vessel being accessed is accomplished by merely subjecting the blood stream to contact with the agent rather than by relying on diffusion across a membrane and subsequent diffusion in the blood stream. The effects of this contact are predominantly in situ or local effects.

When the physiologically active agent is heparin, in situ prevention of clot formation is preferably achieved by subjecting the blood stream to contact with heparin in a heparin immobilizing biocompatible material at the delivery end of the impermeable occlusal balloon. Heparin immobilizing materials include polyvinyl alcohol; surface-modified polymeric biomaterials with poly(ethylene oxide), albumin, and heparin; derivatized dextrins; polymers with hydrophilic spacers; vinyl-pyridine-grafted styrene-butadiene-styrene triblock copolymer; and dimethyl-amino-ethyl-methacrylate-grafted styrene-butadiene-styrene triblock copolymer.

Furthermore, a multifunctional thrombo-resistant coating can be incorporated on the delivery end of an occlusal balloon. Such a coating may include a siloxane surface onto which a plurality of amine functional groups have been bonded. Covalently bonded to the amine functional groups are a plurality of poly(ethylene oxide) chains, such that a single poly(elthylene oxide) chain is bonded to a single amine functional group. A plurality of different bioactive molecules, designed to counteract specific blood-material incompatibility reactions, are covalently bonded to poly(ethylene oxide) chains, such that a single bioactive molecule is coupled to a single poly(ethylene oxide) chain. Methods of manufacturing these materials have been previously described. See, for example, International Patent Applications Nos. PCT/US89/01853 and PCT/US91/02415, which are herein incorporated by reference in their entirety. The resulting siloxane that is so manufactured contains a plurality of different bioactive molecules capable of reacting with blood components which come in proximity to the siloxane surface in order to resist blood-material incompatibility reactions.

In the preferred embodiments of the occlusal balloon of this invention with a semipermeable membrane, the physiologically active agent is effective at the release site, namely in situ. The dosage can be regulated so that the active agent is effective systemically because the active agent circulates with the blood stream. This type of sources of physiologically active agents are herein described as permeating sources of physiologically active agents and they may be utilized with any of the embodiments disclosed herein. The dose required to achieve the anticoagulant effect locally is much less than a systemically therapeutic dose, thus the long term risk associated with in situ effects is less than the risk associated with full systemic anticoagulation.

When the physiologically active agent is provided by immobilizing it on an impermeable occlusal balloon, the active agent is predominantly effective in situ, at or near the contact site. Such sources of physiologically active agents are herein described as in-situ sources of physiologically active agents. They include embodiments of the delivery end of an occlusal balloon on which the physiologically active agent is attached at the outer surface that is exposed to the blood flow.

In addition, other embodiments of this invention incorporate an impermeable balloon that provides a source of at least one physiologically active agent whose effects are manifested in situ and systemically without transport across a semipermeable membrane. In these embodiments, the physiologically active agent is typically released by a substance that is incorporated on the delivery end of the occlusal balloon that is exposed to the blood flow. This type of sources of physiologically active agents are herein described as nonpermeating sources of physiologically active agents. For example, when the physiologically active agent is an anticoagulant, nitrogen oxide releasing polymers can be incorporated on the delivery end of the occlusal balloon so that NO is released into the blood stream. Examples of NO-releasing polymers include diazeniumdiolates added to plastics such as polyvinylchloride and polyurethane. In this case, diazeniumdiolates include specific compounds such as sodium 1-(N,N-diethylamino)diazen-1-ium-1,2-diolate, disodium 1-[2(S)-carboxylatopyrrolidin-1-yl]diazen-1-ium-1,2-diolate, sodium 1-(piperazin-1-yl)diazen-1-ium-1,2-diolate, and 1-{N-methyl-N-[6-(N-methylammonio)hexyl]amino}diazen-1-ium-1,2-diolate.

The features of each one of the herein described embodiments of the occlusal balloon are not meant to be exclusive of features of other embodiments that can be incorporated in the same occlusal balloon to render a functional combination. For example, an occlusal balloon with a semipermeable membrane can also incorporate a source of a physiologically active agent for predominantly in-situ effects, and/or incorporate a source of a physiologically active agent for in situ and systemic effects of the type described in relation to embodiments of nonpermeable occlusal balloons.

Figure 3:
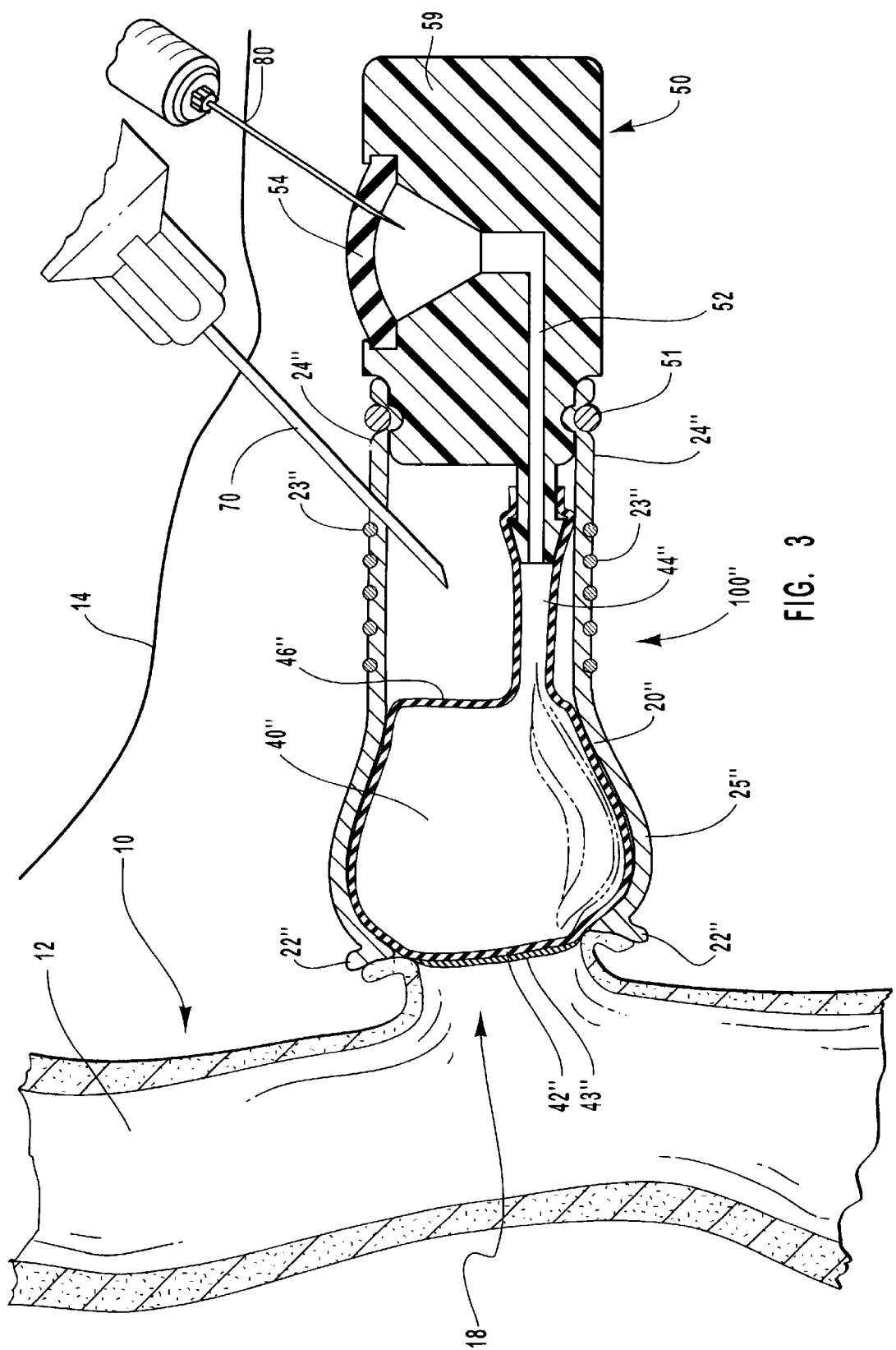
FIG. 3 is a partial cross sectional view of another embodiment of a vascular access system with a reinforced graft vessel that has an enlarged portion, and an occlusal balloon with a semipermeable membrane.

FIG. 3 depicts an occlusal balloon 40" that has a semipermeable membrane laminated onto a balloon that has holes in its delivery end 42" to permit the semipermeable membrane 43" to be contacted through the balloon. Since delivery end 42" is perforated and adjacent to a suitable semipermeable membrane 43", a substance that is to be delivered into the blood stream can pass through the perforations at delivery end 42", reach semipermeable membrane 43", and diffuse into the blood stream through the pores of semipermeable membrane 43". Instead of perforations, occlusal balloon material can have at delivery end 42" any other feature that performs the same function that is performed by perforations, namely allowing for the passage of fluid from and towards semipermeable membrane 43". Note that while a balloon such as balloon 40" prevents the formation of blood clots by exposing blood flowing in lumen 12 in the region near to delivery end 42" to an anticoagulant agent, other agents may also be delivered instead of, or in addition to, an anticoagulant agent.

In addition to coagulation, blood flow stagnation in the region near anastomosis site 18 must be minimized and it is preferably avoided. To this end, occlusal balloon 40" is so configured as to be able to seal the anastomosis site in a way such that no significant cavity is formed at anastomosis site 18. As indicated regarding the embodiment shown in FIG. 1A or in FIGS. 2A–2B, the presence of a cavity or substantially recessed space in this region may lead to blood flow stagnation, clot formation, and, in arteries, formation of unacceptably turbulent blood flow.

Graft vessel 20" as shown in the embodiment depicted in FIG. 3 is preferably provided with an enlarged portion 25" near anastomosis end 22". This enlarged portion provides a recessed space into which delivery end 42" and semipermeable membrane 43" collapse when occlusal balloon 40" is deflated. Like graft vessel 20', graft vessel 20" has conventional reinforcements such as fluorinated ethylene-propylene (FEP) strands bonded onto a PTFE graft vessel identified at 23". Note, however, that while reinforcement 23' extends along the entire length of graft vessel 20', reinforcements 23" terminate before reaching the enlarged portion 25". Reinforcements 23' and 23" are preferably embedded into the material, for example PTFE, of which graft vessel 20" is made, but they can also be partially embedded or externally disposed on graft vessel 20" and attached thereto. Instead of spirals, these reinforcement structures can be embodied by rings, longitudinal features aligned with the longitudinal axis of the occlusal balloon, longitudinal features that present any one amongst a variety of possible chiral configurations, criss-cross stripes, or any other reinforcement pattern that is known to provide structural reinforcement to a flexible, generally cylindrical body. Embodiments of these reinforcement structures are preferably made of plastic. Examples of reinforced PTFE graft material such as graft vessel 20' includes IMPRA® prosthetic vascular grafts from Impra, Inc. of Phoenix, Ariz. or C. R. Bard, Inc. of Murray Hill, N.J., MEDOX™ grafts from Boston Scientific and is also sold by W. L. Gore, of Phoenix, Ariz.

Typical embodiments of this invention are configured to be adapted to an anastomosis fenestra of about 4 mm, in which case the internal diameter of the graft vessel is about 6 mm. Embodiments of the graft vessel that are provided with an enlarged portion such as enlarged portion 25" in FIG. 3 are configured so that the internal diameter of the graft vessel's enlarged portion is between about 8 mm and about 9 mm. A typical length of embodiments of the occlusal balloon from its delivery end to this access end is preferably about 2 cm. The length of the graft vessel is preferably chosen so that it provides a plurality of puncture sites.

Figure 4:
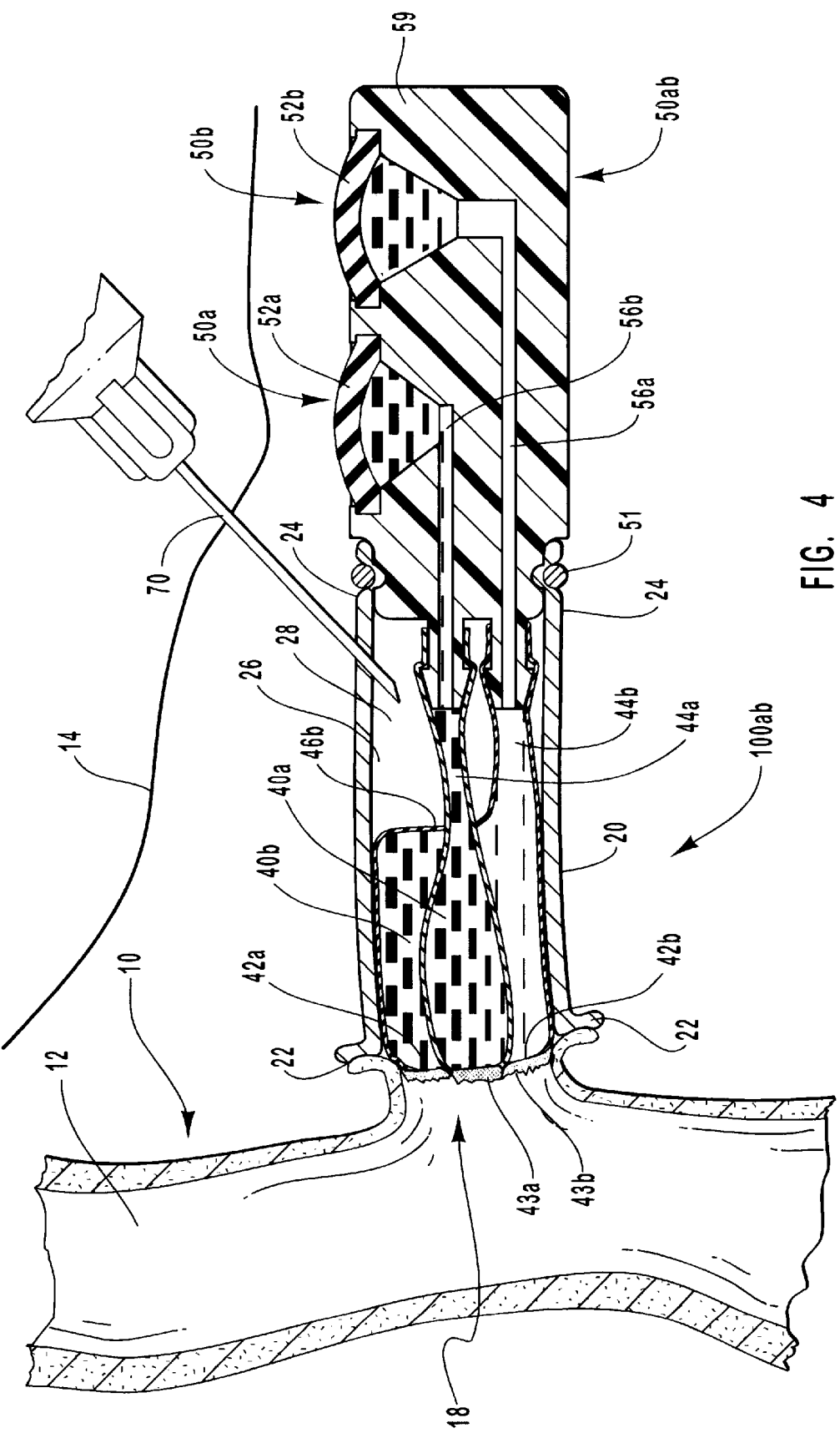
FIG. 4 is a partial cross sectional view of an embodiment of a vascular access system with two occlusal balloons, two semipermeable membranes, and a graft vessel with an enlarged portion. Each balloon is coupled to a separate port device.

Some embodiments of this invention may be provided with more than one occlusal balloon. FIG. 4 shows another exemplary embodiment of the present invention which is provided with two occlusal balloons 40a and 40b. More particularly, graft vessel 20 houses in this particular embodiment first occlusal balloon 40a with first delivery end 42a and first access end 44a, and second occlusal balloon 40b with second delivery end 42b and second access end 44b.

As in the other embodiments, FIG. 4 depicts blood vessel 10 being accessed with the aid of graft vessel 20 that is anastomosed to blood vessel 10 at anastomosis site 18. Blood flowing in lumen 12 is exposed in the region near to delivery ends 42a and 42b to agents that are provided with the aid of occlusal balloons 40a and 40b. When more than one agent is to be provided, the range of molecular weights of such agents may be so broad that a single membrane might not be adequate for the diffusion of the different agents into the blood stream. Even if a single membrane were adequate, conditions to be satisfied regarding the replacement, mixing and compatibility of the agents might require that they be kept in different occlusal balloons. In the arrangement shown in FIG. 4, for example, occlusal balloon 40a may contain an aqueous solution of albumin and heparin. Heparin would be delivered into the blood stream by diffusion across a semipermeable membrane 43a at delivery end 42a and the balloon would be kept inflated by osmotic pressure due to the diffusion of an aqueous fluid across the same membrane into the interior of occlusal balloon 40a. Occlusal balloon 40b can contain a solution of one or more physiologically active agents, such as medications, that can be delivered into the blood stream by diffusion across a semipermeable membrane 43b at delivery end 42b. So if one balloon delivers heparin then the other balloon may be utilized for slow diffusion of small molecular weight solutes, such as medication that requires parenteral administration, including antibiotics, small peptides, and hormones. The embodiment shown in FIG. 4 and equivalents thereof are preferred embodiments for long term peripheral vascular access, particularly for venous access for parenteral medication.

Delivery ends 42a and 42b of occlusal balloons 40a and 40b are so configured as to be able to seal the anastomosis site in a way such that no significant cavity is formed at anastomosis site 18. As indicated regarding the other embodiments, the presence of a cavity or substantially recessed space in this region may lead to blood flow stagnation or to the formation of unacceptably turbulent blood flow, both of which would be expected to predispose to thrombosis. Note that the graft vessels utilized with any of the embodiments disclosed herein may be straight, have an enlarged portion or having any suitable configuration. Accordingly, the graft vessel utilized with balloons 40a and 40b may have an enlarged portion near anastomosis end 22 like enlarged portion 25" shown in the embodiment depicted in FIG. 3. Such an enlarged portion provides a recessed space for accommodating collapsing delivery ends 42a and 42b as occlusal balloon 40b is deflated, and if necessary occlusal balloon 40a. Deflation of occlusal balloon 40b is accompanied when necessary by deflation of occlusal balloon 40a.

The exemplary embodiment of port devices 50a and 50b shown in FIG. 4, also referred to as multiple port device 50ab, have components that are identical to those of the other port devices except that there are two separate port devices in port housing 59. Self-sealing covers 52a and 52b may be arranged relative to each other in a variety of ways. For example, they can be located next to each other and aligned on the same side of port device 50ab as shown in FIG. 4, or they can be located at any desired angle relative to each other and facing along different axial directions. In addition to multiple port devices that are coupled to multiple balloons, it is also possible to utilize multiple port devices that are in fluid communication so that fluid may be delivered into a single balloon from one of multiple port devices. While self-sealing covers 52a and 52b can be repeatedly penetrated by a hypodermic needle or a similar medical instrument used to inject fluid into or to draw fluid from a cavity, they do eventually require replacement. To delay the need for such replacement, multiple port devices may be provided having conduits that are in fluid communication and that terminate at a single common coupler 58.

Port devices according to this invention can also be embodied by port devices that have additional ports for conventional uses, such as ports that are configured to operate probes, sampling devices, imaging devices and imaging device elements, or medical intervention assisting devices.

It is understood that configurations of balloons 40a and 40b that depart from that shown in FIG. 4 while including the basic elements therein shown are within the scope of this invention. For example, access conduits or ends 44a and 44b can in some embodiments be flush with respect to each other, or balloon 40b can in some embodiments be contained within balloon 40a. In other embodiments, balloons 40a and 40b are placed within the graft vessel essentially next to each other, in which case the balloon that is located closer to the port device preferably has an elongated delivery end that extends substantially up to the anastomosis site. Either one of access conduits or ends 44a or 44b, or both access ends, can in some embodiments extend back to the port device and be in contact engagement with such port device, particularly in the inflated configuration. Balloon 40a may be located in the space between chamber portion 46b and the port device, which is chamber 28 within lumen 26, as shown or in a less obtrusive configuration.

It is also understood that elements of any embodiment of the vascular access system according to this invention may be provided with suitable radio-opaque markings so that its location or particular configuration can be externally observed. This markings can be particularly useful when incorporated in the vascular graft or in the occlusal balloon.

Figure 5A:
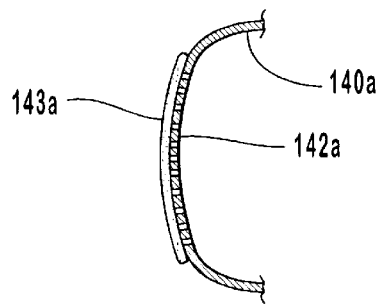
FIGS. 5A–5D schematically illustrate different configurations of a semipermeable membrane at the delivery end of an occlusal balloon.

FIG. 5A depicts a cross-sectional view of a balloon 140a that is similar to balloon 40" as it has a portion with holes formed therethrough and a semipermeable membrane 143a is laminated onto the portion of balloon 140a that has holes.

Semipermeable membranes used in different embodiments of this invention can be attached to the delivery end of the occlusal balloon with or without a backing that provides structural support, depending on the type of membrane being used. Also, the occlusal balloon material at the delivery end can in some embodiments provide structural support to the semipermeable membrane or vice versa.

Figure 5B:
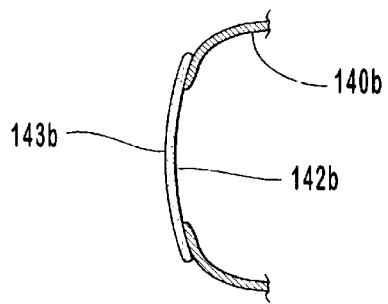
Figure 5C:
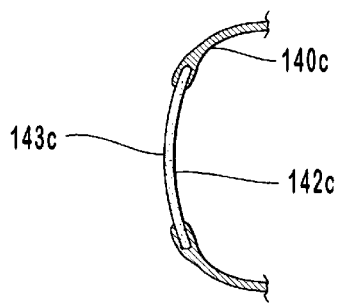
Figure 5D:
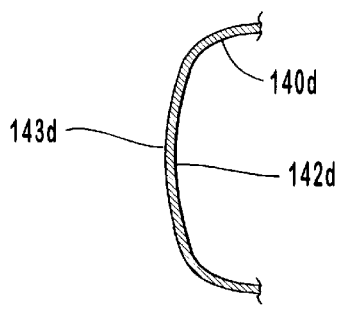

FIGS. 5B and 5C respectively depict cross-sectional views of a semipermeable membrane 143b and 143c attached to an occlusal balloon 140b and 140c like semipermeable membrane 43' shown in FIGS. 2A–2B. Occlusal balloon 140b has a delivery end 142b onto which semipermeable membrane 143b is attached. Occlusal balloon 140c is provided with features that brace the edges of semipermeable membrane 143c. FIG. 5D depicts an occlusal balloon 140d like occlusal balloon 40 that has an integral semipermeable region 143d. In one embodiment, balloon 140d is made of, for example, PTFE that is impermeable to the solvent and solute or solutes in the occlusal balloon, and the delivery end of the balloon is made of porous PTFE that embodies semipermeable region 143d.

In addition to single layer and bi-layer configurations described above for the disposition of the semipermeable membrane at the delivery end of the occlusal balloon, other configurations are also possible. These additional configurations include a tri-layer configuration and configurations in which the semipermeable membrane is sandwiched between two layers of material, one at each side of the membrane, that allow for the passage of fluid from and to the membrane.

Preferably, the shape of the functional portion of the semipermeable membrane used in some embodiments of this invention is generally circular, in which case corresponding features at the delivery end of the occlusal balloon are also generally circular. These shapes, however, are not unique or determinative of the characteristics and functions of the vascular access device of this invention, and other geometrical shapes can also be used, particularly when the base materials or manufacturing tools can more efficiently be used with noncircular membranes.

The occlusal balloon of specific embodiments of this invention at its delivery end and the membrane or membranes therein located present a generally curved surface that slightly protrudes out of the occlusal balloon's body. This generally curved surface is preferably convex on the side exposed to the blood stream of the blood vessel being accessed. This preferred shape is consistent with the slightly greater pressure within the occlusal balloon relative to the vascular pressure in the blood vessel being accessed by an embodiment of a device according to this invention.

Figure 6A:
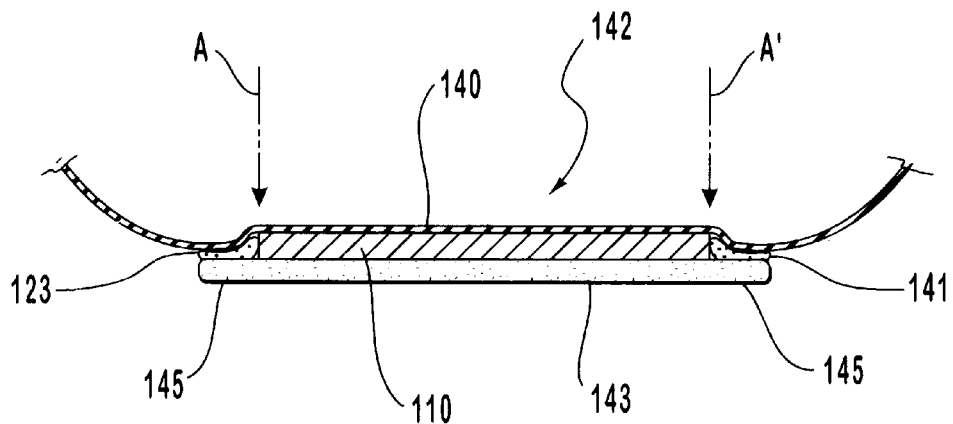
FIGS. 6A–6B schematically illustrate several steps in a technique to attach a semipermeable membrane to the delivery end of an occlusal balloon.
Figure 6B:
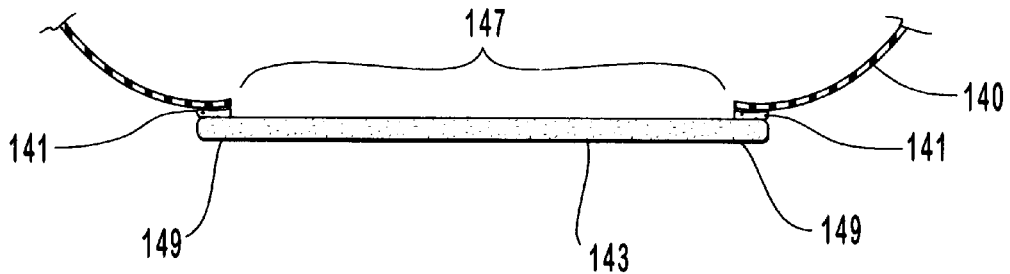

Although a variety of techniques can be relied on to attach a semipermeable membrane to the delivery end of an occlusal balloon as shown in FIG. 5B, a preferred technique comprises the steps of placing a protective material 210 between occlusal balloon delivery end 142 and semipermeable membrane 143 and bonding, preferably with a biocompatible adhesive, contour 145 of semipermeable membrane 143 to the terminal end of the occlusal balloon as schematically shown in FIG. 6A. Occlusal balloon material 140, which may be formed from expandable material such as silicone or latex, is subsequently cut as indicated by broken arrows A–A', thus obtaining the type of configuration shown in FIG. 6B, where functional region 147 of the semipermeable membrane is typically surrounded by small nonfunctional portions 149 bound to the occlusal balloon material by an adhesive 141.

FIGS. 7A–7B depict an occlusal balloon 240 that extends integrally from a graft vessel 220. FIGS. 8A–8K describe methods for manufacturing and utilizing such an integral occlusal balloon 240 and graft vessel 220. The embodiment shown in FIGS. 7A–7B is best understood after review one of the manufacturing methods as shown in FIGS. 8A–8K.

Figure 8A:
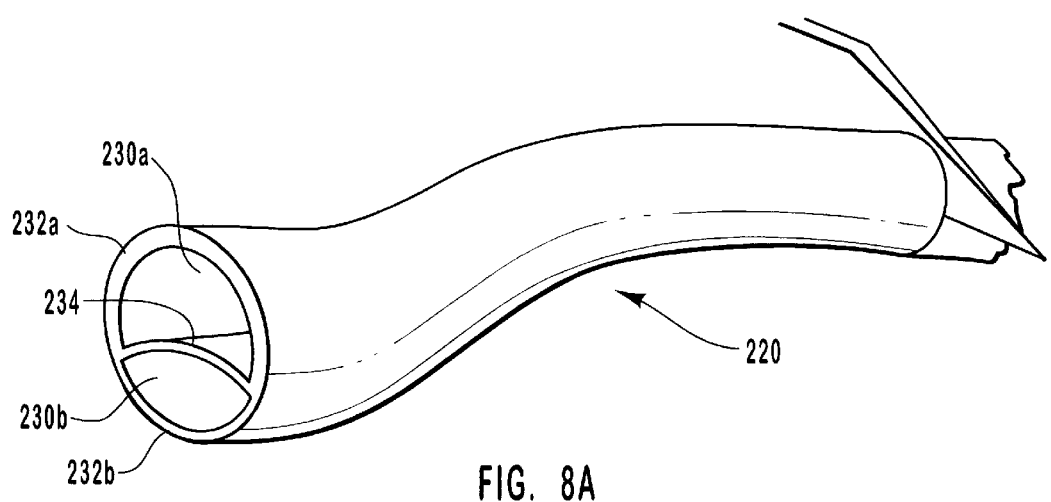
FIG. 8A is a perspective view of a dual lumen graft vessel.
Figure 8B:
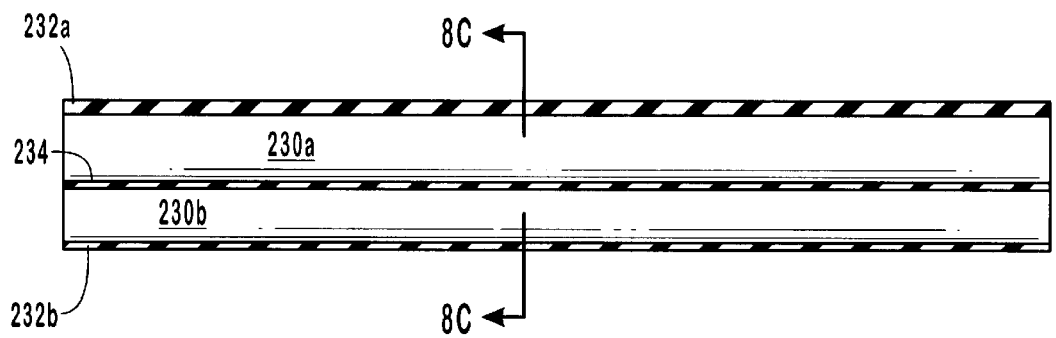
FIG. 8B is a longitudinal cross sectional view of the embodiment shown in FIG. 8A.
Figure 8C:
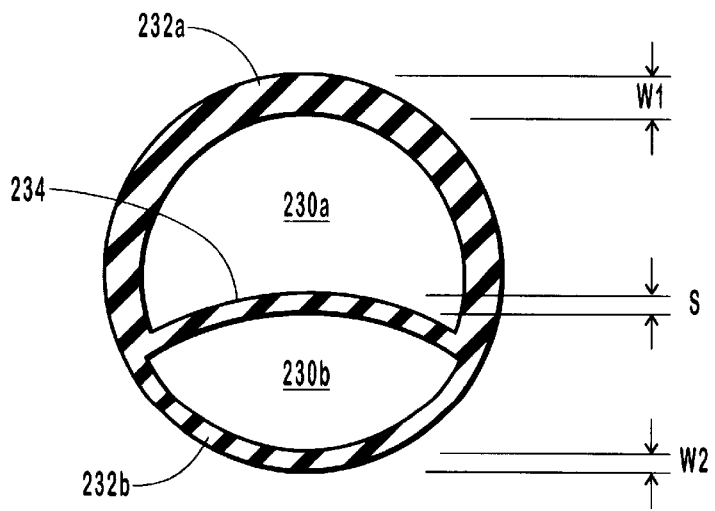
FIG. 8C is a transverse cross sectional view of the embodiment shown in FIG. 8A taken along cutting lines 8C—8C in FIG. 8B.

FIG. 8A depicts a dual lumen graft vessel 220 being cut into a section having a desired length. Dual lumen graft vessel 220 has two lumens 230a and 230b that are divided by a septum 234. These same features are shown in FIGS. 8B–8C which respectively provide a longitudinal cross-sectional view and a transverse cross-sectional view taken along cutting line 8C—8C. As shown in FIG. 8C, the wall 232a of first lumen 230a has a wall thickness identified as W1 that is approximately equal to the combined thickness of the septum 234, identified as S, and the thickness of the wall 232b of lumen 230b identified as W1. The benefits of these relative thickness are described below.

Figure 8D:
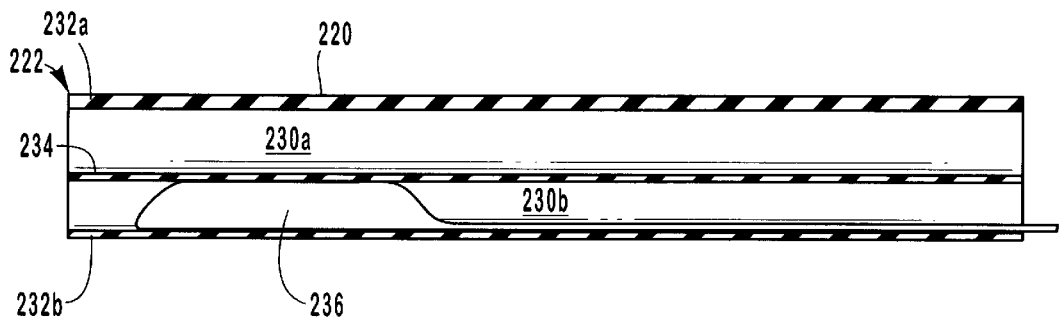
FIG. 8D is a longitudinal cross sectional view of the embodiment shown in FIG. 8A with the septum and the wall of one of the lumens joined together at the anastomosis end.

Septum 234 and the wall 232b of second lumen 230b are joined together at anastomosis end 222 before or after an expandable balloon 236 is positioned in second lumen 230b as shown in FIG. 8D. Septum 234 and the wall 232b of second lumen 230b may be joined together by any suitable means such as heat fusing them together or by applying an adhesive or an appropriate solvent at anastomosis end 222. For example, septum 234 and wall 232 may be joined by being soaked or coated with a solution that fills the pores or passageways of the PTFE. The solution may, for example, comprise polyurethane soaked in tetrahydrofuran. The solution fills the pores and then the tetrahydrofuran evaporates leaving the polyurethane. Note that as shown in FIG. 8G, a transverse cross-sectional view taken along cutting line 8G—8G, after the portion of septum 234 and the portion of the wall 232b of second lumen 230b have been joined at anastomosis end 222 then the wall thickness is about the same around the perimeter of vessel 220 at anastomosis end. More particularly, since the combined thickness of septum 232 and the wall 232b of second lumen 230b approximately equal the wall thickness of the wall 232a of lumen 230a, graft vessel 220 now has a wall thickness at its anastomosis end 222 that is about the same.

Figure 8E:
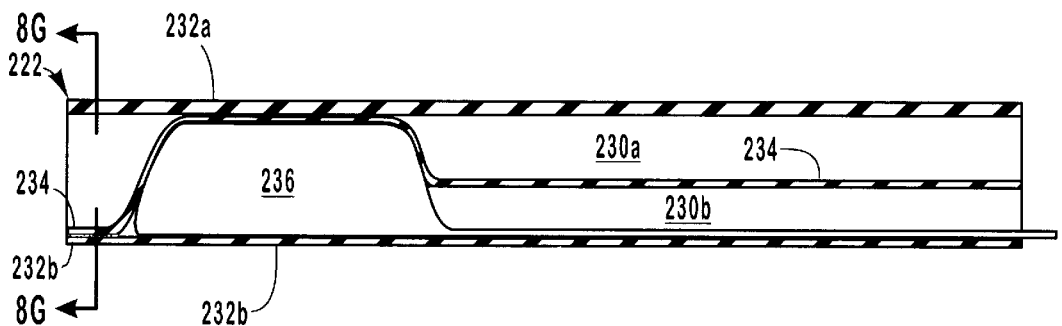
FIG. 8E is a longitudinal cross sectional view of the embodiment shown in FIG. 8A showing the septum being stretched by an expandable balloon.

FIG. 8E depicts expandable balloon 236 stretching septum 234 at the anastomosis end 222 of graft vessel 220. Graft vessel 220 is preferably formed from expanded PTFE that is generally impermeable to a particular physiologically active agent such as heparin until it is stretched. For example, the expanded PTFE may be Gore-Tex® material obtained from W. L. Gore & Associates, of Newark, Del. Note that expandable balloon 236 is designed to stretch septum 232 primarily toward anastomosis end 222 since this portion of septum 232 eventually becomes semipermeable region 243 of balloon 240. The portions of septum 234 and wall 232b of second lumen 230b that are joined together may be clamped or held during the stretching procedure to insure that they are not separated.

Figure 8F:
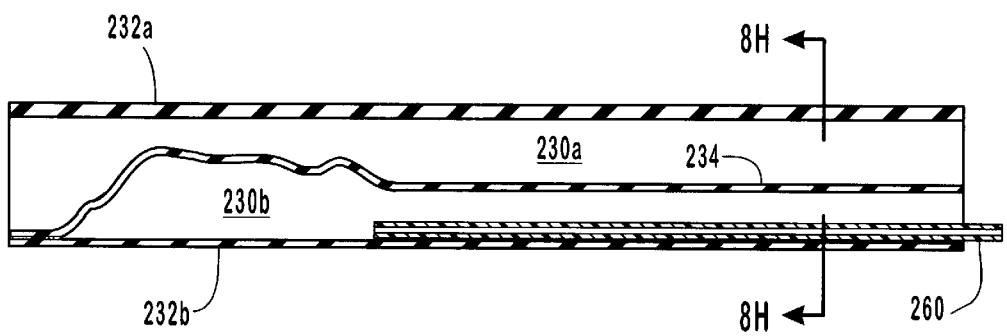
FIG. 8F is a longitudinal cross sectional view of the embodiment shown in FIG. 8A showing a tube being placed in the first lumen.
Figure 8G:
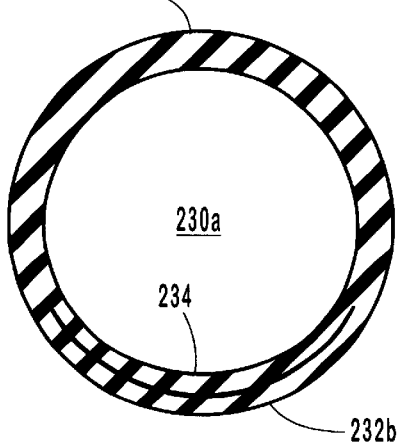
FIG. 8G is a transverse cross sectional view of the embodiment shown in FIG. 8A taken along cutting lines 8G—8G in FIG. 8D.
Figure 8H:
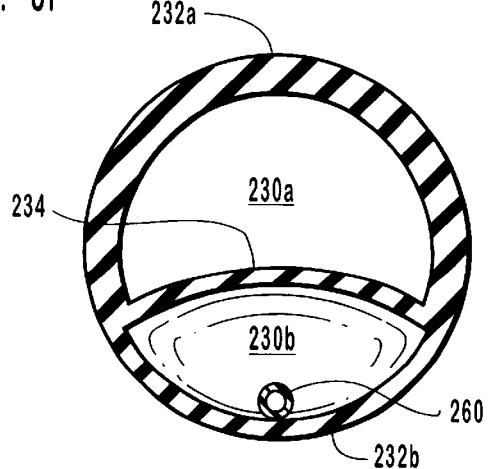
FIG. 8H is a transverse cross sectional view of the embodiment shown in FIG. 8A taken along cutting lines 8H-H in FIG. 8F.

FIG. 8F shows the placement of a tube 260 within second lumen 230b after expandable balloon 236 has been removed. FIG. 8H provides a transverse cross-sectional view taken along cutting line 8H—8H in FIG. 8F that depicts the position of tube 260 in second lumen 230b. Note that second lumen 230b is smaller than first lumen 230a. While this provides sufficient room for septum 234 to be stretched upward into first lumen 230a, it is not required and other configurations are possible. Similarly, septum 234 need not necessarily be arched upward as shown since it may be straight or have an opposite curved orientation such that it curves toward the wall 232b of second lumen 230b.

Figure 8I:
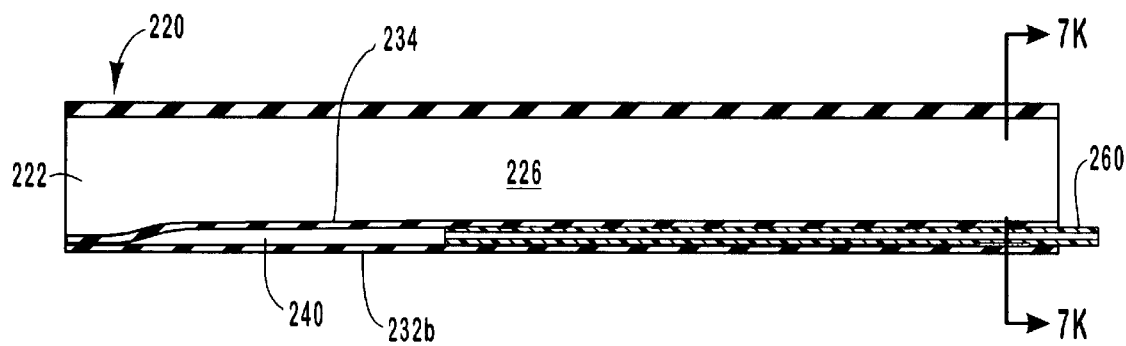
FIG. 8I is a longitudinal cross sectional view of the embodiment shown in FIG. 8A showing the septum joined to the wall of the first lumen around the tube.
Figure 8J:
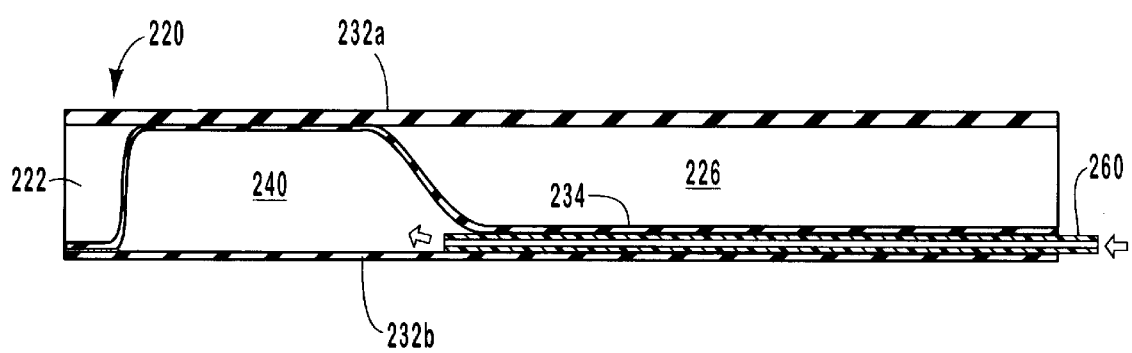
FIG. 8J is a longitudinal cross sectional view of the embodiment shown in FIG. 8I showing fluid being delivered through the tube to inflate the balloon.
Figure 8K:
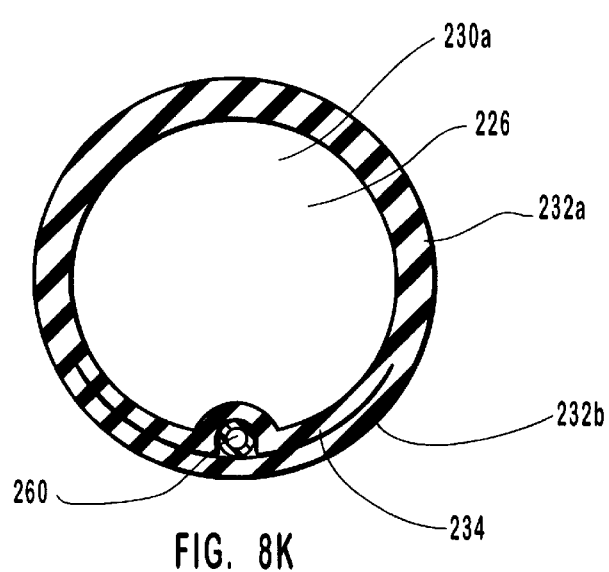
FIG. 8K is a transverse cross sectional view of the embodiment shown in FIG. 8I taken along cutting lines 8K—8K in FIG. 8I showing the septum joined to the wall of the first lumen around the tube.

FIG. 8I shows septum 234 joined to the wall 232b of second lumen 230b around tube 260 such that only a portion of first lumen 230b remains which is the occlusal balloon identified at 240. FIG. 8K provides a transverse cross-sectional view taken along cutting line 8K—8K in FIG. 8I that depicts the position of septum 234 around tube 260 and against the wall 232b of second lumen 230b. Note that since there is now only a single lumen in the graft vessel, first lumen 230a becomes lumen 226 of graft vessel 220. FIG. 8J depicts balloon 240 being inflated from a fluid received via tube 260.

One advantage of the configuration shown in FIG. 7A is that chamber 228 can be relatively large. The length of chamber 228 permits device or system 200 to be utilized for a long period of time. Additionally, tube 260 is resistant to be punctured by needle 70 as needle 70 is introduced into lumen 226, or more specifically chamber 228. Tube 260 is preferably formed from a nickel/titanium alloy as such alloys are flexible and have memory. However, tube 260 can be formed from any suitable material such as metals and plastics.

Another advantage of apparatus 200 is the ability of balloon 240 to remain in position. More particularly, since occlusal balloon 240 and graft vessel 220 are integral, occlusal balloon 240 cannot migrate out of the graft vessel and into the blood vessel over time as the balloon is repeatedly inflated and deflated and as fluid is flushed through graft vessel 220 over the deflated balloon. When the occlusal balloon and the graft vessel are not integral, it may be necessary in some instances to prevent the occlusal balloon from migrating out of the graft vessel and into the blood vessel. Such migration can be prevent by deploying an appropriate stent at the anastomosis site with the balloon abutting the side of the stent. An example of an appropriate stent is disclosed in U.S. Pat. No. 5,456,712 issued to Maginot.

As discussed in reference to FIG. 8G, the wall thickness is approximately the same around the perimeter of the graft vessel at the anastomosis end after septum 234 and lumen wall 232b are joined together. Above the anastomosis end 222, tube 260 causes lumen wall 234 to slightly protrude into lumen 226 as shown FIG. 8K. However, as shown, in FIG. 8I, when balloon 240 is deflated lumen 226 is quite accessible and generally has the same shape along its length. This configuration is useful for joining graft vessel 220 to blood vessel 10 via a compression plate apparatus as shown at 300 in FIGS. 2A–2B or 300' in FIGS. 7A–7B. Details regarding compression plate apparatus 300' are provided in copending U.S. patent application Ser. No. 09/737,200 which is entitled Compression Plate Anastomosis Apparatus and Related Systems and which was filed on Dec. 14, 2000. Details regarding compression plate apparatus 300 are also provided in Ser. No. 09/737,200 as well as copending U.S. patent application Ser. No. 09/460,740 which is entitled Compression Plate Anastomsosis Apparatus and which was filed on Dec. 14, 1999. Methods, systems and devices for anastomosing a graft vessel to a blood vessel are also disclosed in U.S. patent application Ser. No. 09/293,336 which is entitled Methods, Systems and Apparatus for Intraluminally Directed Vascular Anastomosis and which was filed on Apr. 16, 1999. These applications are herein incorporated by reference in their entirety. The present invention, however, does not require a specific anastomosis technique for its implementation. Accordingly, no specific structure is shown for joining the graft vessel to the blood vessel in many of the drawings.

Like the other balloons discussed above, a balloons that extends integrally from a vessel may be formed such that the balloon is impermeable. Additionally, a balloon that extends integrally from a vessel may be formed by any suitable method and from any appropriate material. For example, a dual lumen graft vessel may be formed from a type of PTFE that is penetratable by heparin and which is subsequently treated to be nonpermeable throughout its length except at the delivery end of the balloon. More particularly, a dual lumen balloon may be formed as shown in FIG. 8A except the septum may extend beyond the walls of the lumens. A tube may be adhered in place between the septum and the lumen walls of the bottom lumen such as is shown in FIG. 8I. With the exception of the portion of the septum extending beyond the lumens, the remainder of the dual lumen vessel can be treated with a solution that fills its pores such as polyurethane soaked in tetrahydrofuran, as discussed above. The portion of the septum extending beyond the lumen walls is then attached to the walls of bottom lumen to form an occlusal balloon.

Figure 9:
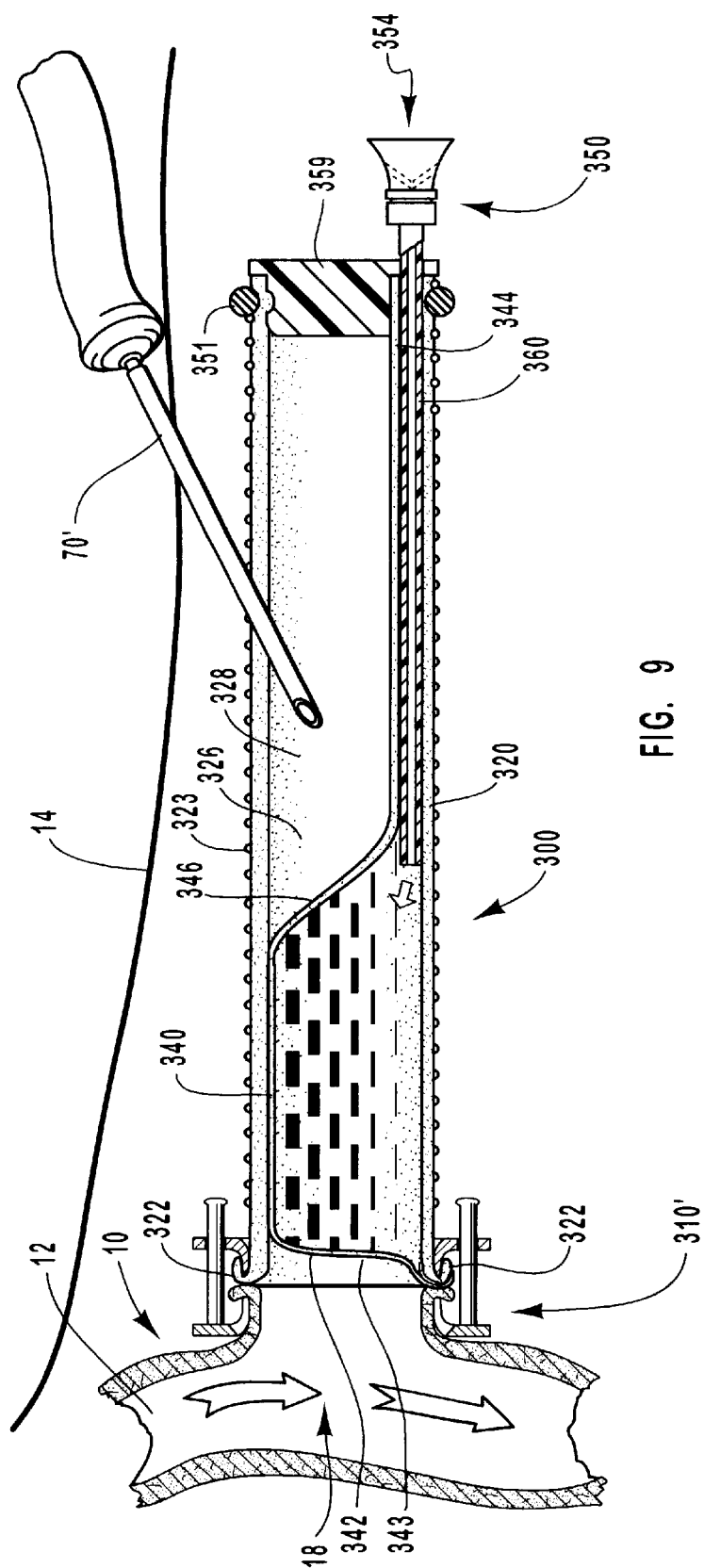
FIG. 9 is a partial cross sectional view of an embodiment of a vascular access system with an occlusal balloon that has a valved coupler port.

FIG. 9 depicts another embodiment at 300. Balloon 340 is coupled via a coupling tube 360 that terminates at a coupler port 350, another embodiment of a port device. Coupler port 350 is adapted to couple with a needle in a manner such that fluid can be delivered into balloon 340 or drawn from balloon 340. Coupler port 350 has a funnel shaped chamber 354 that is adapted to direct the needle toward a valve 352 shown in dotted lines that can be penetrated by the needle in order to provide fluid communication with balloon 340. A coupler may also be rotated by a needle that is uniquely adapted to engage the coupler by rotating coupler into an open position for fluid communication. A stop 359 is positioned at the port end 324 of graft vessel 320 that seals the graft vessel due to the compression of o-ring 351. In another embodiment, the balloon is directly inflated and deflated by puncturing the balloon through the wall of the graft vessel with a small needle. Similarly, the balloon communication with a fluid chamber that extends a certain length within the graft vessel and acts as a port device. Such a fluid chamber may be defined by the same material as the graft vessel.

A vascular access with a system according to this invention is preferably created by first performing a vascular anastomosis to attach a graft vessel to the blood vessel that is being accessed, and then placing an occlusal balloon within the graft vessel. This occlusal balloon may be provided with a port device already attached to it, or the port device may be subsequently attached to the occlusal balloon by conventional techniques. Once a vascular access system according to this invention is placed at the access site, the entire system preferably remains subcutaneously placed for its use in procedures such as dialysis, in particular hemodialysis, and drug delivery. In addition to hemodialysis, other examples of useful external blood treatments that can be performed with the present invention include plasmapheresis, cytopheresis, hemodialysis, apheresis, hemoperfusion, and hemofiltration. Examples of such external treatment methods are provided in greater detail in U.S. patent application Ser. No. 09/481,283 entitled Methods for External Treatment of Blood filed on Jan. 11, 2000, which was previously incorporated by reference.

Figure 10:
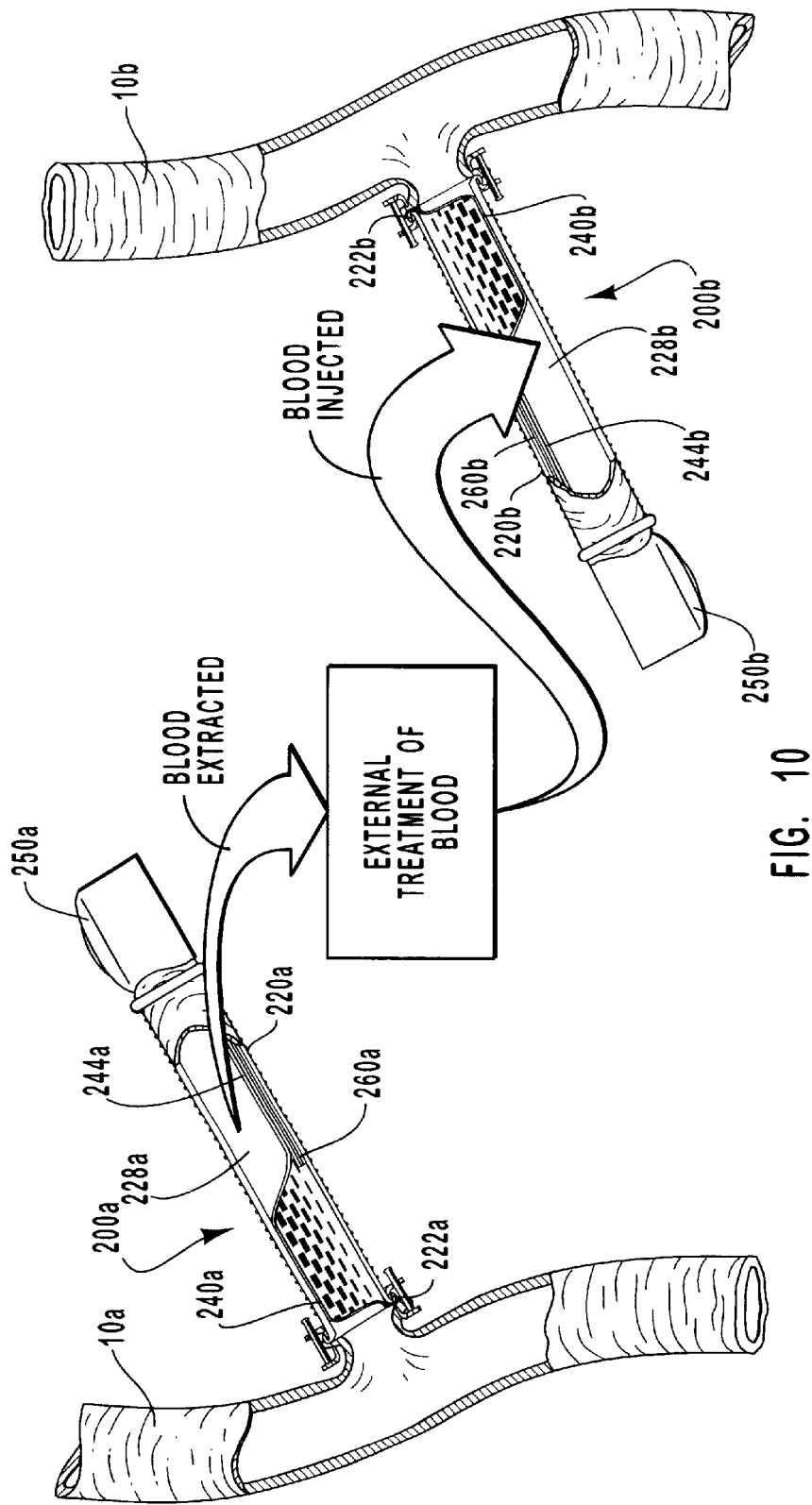
FIG. 10 schematically shows the practice of hemodialysis with an occlusal balloon in a graft vessel.

FIG. 10 schematically illustrates an embodiment of a method for externally treating blood according to this invention. In the example shown in FIG. 10, blood is extracted through an extraction vascular access apparatus such as the embodiment of extraction vascular access apparatus 200a, and delivered through a delivery vascular access apparatus such as the embodiment of delivery vascular access apparatus 200b. Note that extraction vascular access apparatus 200a and delivery vascular access apparatus 200b are both identical to the apparatus shown in FIGS. 7A–7B. Because the vascular access apparatus of this invention permits multiple vascular access, whether any given vascular access apparatus is employed in any specific treatment episode as an extraction or a delivery apparatus is a matter of convenience and choice. In addition, once blood has been extracted through an extraction vascular access apparatus and there is an available delivery vascular access apparatus to return the blood flow to a blood vessel, such extracted blood can be subjected to a hemodialysis or to any other blood treatment. Consequently, the term "hemodialysis" in the context of this invention is understood to broadly refer to external treatment of blood, including an actual hemodialysis treatment, and any other treatment of blood that is performed outside a patient's body, and which requires the extraction, treatment and subsequent delivery of the treated blood to the patient.

Blood vessels 10a and 10b represent the blood vessels involved in the treatment process. When blood is extracted from blood vessel 10a, it is subjected to treatment, and it is subsequently returned to blood vessel 10b, blood vessel 10a is referred to as the extraction blood vessel and blood vessel 10b is referred to as the delivery blood vessel. Although the apparatus, systems and methods of this invention are suitable for the practice of a variety of external treatments of blood, they are particularly suitable for the practice of vein-to-vein hemodialysis. In this case, blood vessels 10a and 10b would represent the vein from which blood is extracted and the vein to which dialyzed blood is injected, respectively.

An embodiment of an apparatus or system according to this invention is attached to each one of blood vessels 10a and 10b as schematically shown in FIG. 10 by embodiments 200a and 200b, respectively. These embodiments are anastomosed at sites 222a and 222b, and they can be embodiments of any of the foregoing vascular access devices and systems of this invention and combinations thereof. For the practice of a preferred method according to this invention, these embodiments comprise occlusal balloons 240a and 240b, port devices 250a and 250b, and access conduits 244a and 244b that respectively contain access tubes 260a (not shown) and 260b (not shown).

In some embodiments of this invention, port devices 250a and 250b, together with occlusal balloons 240a and 240b, define respective chambers 228a and 228b. Occlusal balloons 240a and 240b are preferably disposed within graft vessels 222a and 222b in these embodiments so that chambers 228a and 228b allow for the injection therein of a biocompatible fluid, such as isotonic saline solution. In other embodiments of this invention, no significant chamber or significant volume is left between occlusal balloons 240a and 240b and respective port devices 250a and 250b. The volume occupied by distended occlusal balloon 240a, plus optionally the volume of chamber 228a, defines an occludable interior in vascular access apparatus 200a that is configured for receiving a fluid such as blood. Similarly, the volume occupied by distended occlusal balloon 240b, plus optionally the volume of chamber 228b, defines an occludable interior in vascular access apparatus 200b that is configured for receiving a fluid such as blood.

As indicated in the description of preferred embodiments of this invention, graft vessels 222a and 222b and port devices 250a and 250b are self-sealing, so they can be repeatedly accessed without requiring replacement or additional sealing procedures after each treatment episode. Access is preferably performed by appropriately puncturing the graft vessels and port devices as desired. The interior of the occlusal balloon is preferably accessed through the corresponding port device, while the interior of the graft vessel is preferably accessed by directly puncturing the graft vessel wall.

Occlusal balloons that selectively and controllably expose the blood flow in vessels 10a and 10b to a physiologically active agent are preferred for the practice of the methods of this invention. This can be achieved by any of the occlusal balloon embodiments to this effect that have been described hereinabove and their equivalent devices. Vascular access apparatus 200a and 200b preferably remain subcutaneously placed during the practice of hemodialysis and also during the intervening periods between hemodialysis episodes.

Hemodialysis, or any other external blood treatment, is preferably performed according to methods of this invention by extracting blood from blood vessel 10a through vascular access apparatus 200a, having this extracted blood dialyzed, and returning it by injecting it into blood vessel 10b through vascular access apparatus 200b. Extraction of blood is preferably performed with occlusal balloon 240a in a deflated configuration. Similarly, injection of blood is preferably performed with occlusal balloon 240b in a deflated configuration. Because the walls of graft vessels 222a and 222b are repeatedly punctured in repeated hemodialysis episodes, blood vessels 10a and 10b remain viable and unaffected by the repeated access. This procedure facilitates vein-to-vein hemodialysis because the number of venous sites that are available for extended periods of time for the practice of hemodialysis is very limited. Furthermore, the practice of vein-to-vein hemodialysis is a desirable dialysis practice because AV (arterio-venous) graft hemodialysis typically leads to venous hyperplasia and stenosis.

Blood flow into the interior of vascular access apparatus 200a or 200b is achieved by deflating occlusal balloon 240a or 240b, respectively. This can be achieved by drawing the fluid that keeps occlusal balloon 240a in a distended configuration through port device 250a, which is maintained in fluid communication with occlusal balloon 240a through conduit 63. An analogous operation can be performed to achieve blood flow into the interior of vascular access apparatus 200b, which involves the deflation of balloon 240b by drawing fluid through tube 260b in access conduit 244b and through port device 250b. When blood flow into graft vessels 222a and 222b has been allowed, hemodialysis or any other external blood treatment can proceed in a conventional manner. For this purpose, graft vessels 222a and 222b are punctured and blood is allowed to flow from vessel 222a to vessel 222b. When necessary, blood flow is forced with an appropriate pump.

Depending on the specific treatment to which the blood is subjected externally, the device that provides such treatment is part of the fluid communication between the extraction vascular access apparatus and the delivery vascular access apparatus. In certain treatments, such as irradiation, the blood flow is exposed to the treating effects without actually being in fluid communication with the device that provides such effects. Since the blood flow must interact in some external manner with the device that provides the treatment, it is said that the fluid communication between the extraction vascular access apparatus and the delivery vascular access apparatus encompasses communication with a blood treating device.

Examples of external blood treatments that can be performed with the present invention include plasmapheresis, cytopheresis, hemodialysis, apheresis, hemoperfusion, and hemofiltration.

In some of these treatments, such as plasmapheresis—also known as plasma separation or plasma exchange—, whole blood is removed from the body, the bloods cellular components are separated in a blood treatment device, and subsequently reinfused in a saline solution or some other plasma substitute, thus depleting the body's own plasma without depleting its blood cells. In this case, the external treatment of blood is typically performed with a cell separator. Plasmapheresis is currently widely accepted for the treatment of myasthenia gravis, Lambert-Eaton syndrome, Guillain-Barré syndrome, and chronic demyelinating polyneuropathy. An average course of plasma exchanges is six to ten treatments over two to ten weeks, with some centers performing one plasmapheresis session per week and other centers performing more than one session per week. Patients undergoing plasmapheresis are typically administered blood anticoagulant medications, and the blood treatment device includes a plasmapheresis separator. Plasmapheresis and cytopheresis are specific instances of the more general apheresis, which is the withdrawal of whole blood from the body, separation of one or more components, and return by transfusion of the remaining blood to the donor.

Hemoperfusion is the technique of passing blood extracted from the body through an extracorporeal sorbent column for the purpose of removing harmful substances. In one practice of hemoperfusion, blood is passed through a blood treatment device that comprises a biocompatible hemoperfusion cartridge that contains activated carbon adsorbent coated with an antithrombogenic heparin-hydrogel. This technique permits the removal of a variety of toxins in the blood, and it is used in the treatment of drug overdoses, hepatic failure, encephalopathy, and removal of chelated aluminum from hemodialysis patients.

Hemodialysis is one of the more common forms of dialysis conventionally used. In hemodialysis, a hemodialyzer, or artificial kidney, takes the place of failed kidneys which may have lost up to 80 or even 90% of their functions. Patients with chronic kidney or renal failure need dialysis to remove excess urea, fluid, electrolytes, minerals, and other wastes form the blood stream since the kidneys cannot perform this cleansing. In this case, the external treatment of blood is typically performed with a hemodialyzer as a blood treatment device. An ultrafiltration hemodialyzer is a hemodialyzer that uses fluid pressure differentials to typically bring about loss of protein-free fluid from the blood to the bath, as in certain edematous conditions.

With hemofiltration, patients have fluid and waste products removed from the blood at a constant rate, twenty-four hours a day, for as long as necessary, with the aid of a blood treatment device that comprises a hemofiltration cartridge. This technique is typically used on patients for whom hemodialysis is not considered safe, and also to treat conditions such as uremia, acute renal failure, refractory fluid overload, and massive edema.

Embodiments of this invention that are provided with chambers 228a and 228b would in principle permit the puncturing of the corresponding graft vessels prior to the deflation of the corresponding balloons. However, as indicated above, occlusal balloons 240a and 240b are preferably deflated prior to the puncturing of the respective graft vessels 222a and 222b. Similarly, any puncturing device inserted through the walls of graft vessels 222a and 222b is preferably removed prior to the distension of the respective occlusal balloons 240a and 240b.

When a treatment episode is completed, occlusal balloons 240a and 240b are brought back to their distended configurations by inflating them. Inflation is preferably achieved by injecting a fluid through the respective port devices 250a and 250b. These configurations of occlusal balloons 240a and 240b prevent blood flow into the interior of graft vessels 222a and 222b, respectively. With the aid of the same needle that has been used in the practice of hemodialysis or with a different puncturing device, the interior of graft vessels 222a and 222b can be washed and their contents replaced by a biocompatible fluid such as isotonic saline solution.

As indicated above, embodiments 200a and 200b preferably remain subcutaneously placed and ready to be accessed again in another treatment session. As also indicated in the foregoing description of preferred embodiments of this invention, blood flow in vessels 10a and 10b can preferably be exposed to an appropriate physiologically active agent, such as heparin. This exposure is preferably provided during the periods between hemodialysis sessions, so that the formation of blood clots, or any other coagulation-related phenomenon, near the anastomosis sites is significantly reduced.

As indicated in the foregoing description of preferred embodiments of this invention, embodiments 200a and 200b can be additionally used to intravenously deliver medication while at least one of them is anastomosed, and this goal can be achieved too when both embodiments 200a and 200b are anastomosed for hemodialysis.

The sequence of steps related to the expansion/contraction of the occlusal balloons, the replacement of any fluid within graft vessels 222a and 222b, and the optional intravenous delivery of medicine can be performed according to the methods of this invention in any desired biocompatible order.

EXAMPLES OF USE OF OCCLUSAL BALLOONS

Figure 11:
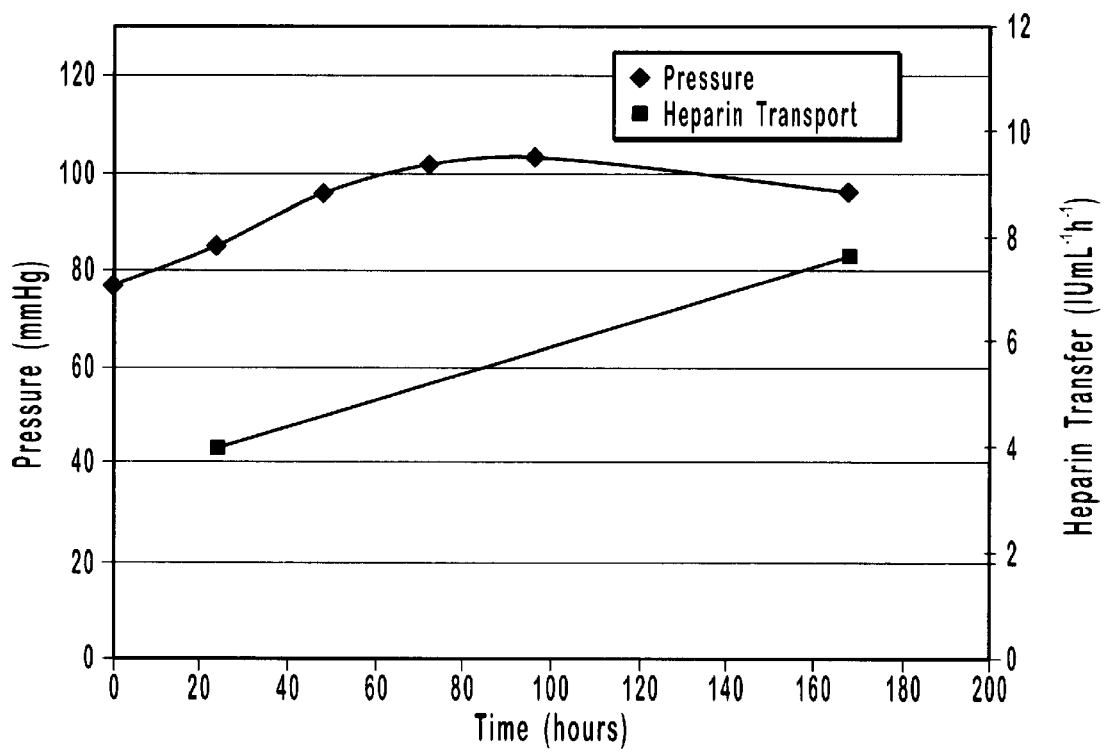
FIG. 11 shows the time evolution of the osmotic pressure and the osmotic pressure and heparin transfer for a heparin aqueous solution with no albumin.
Figure 12:
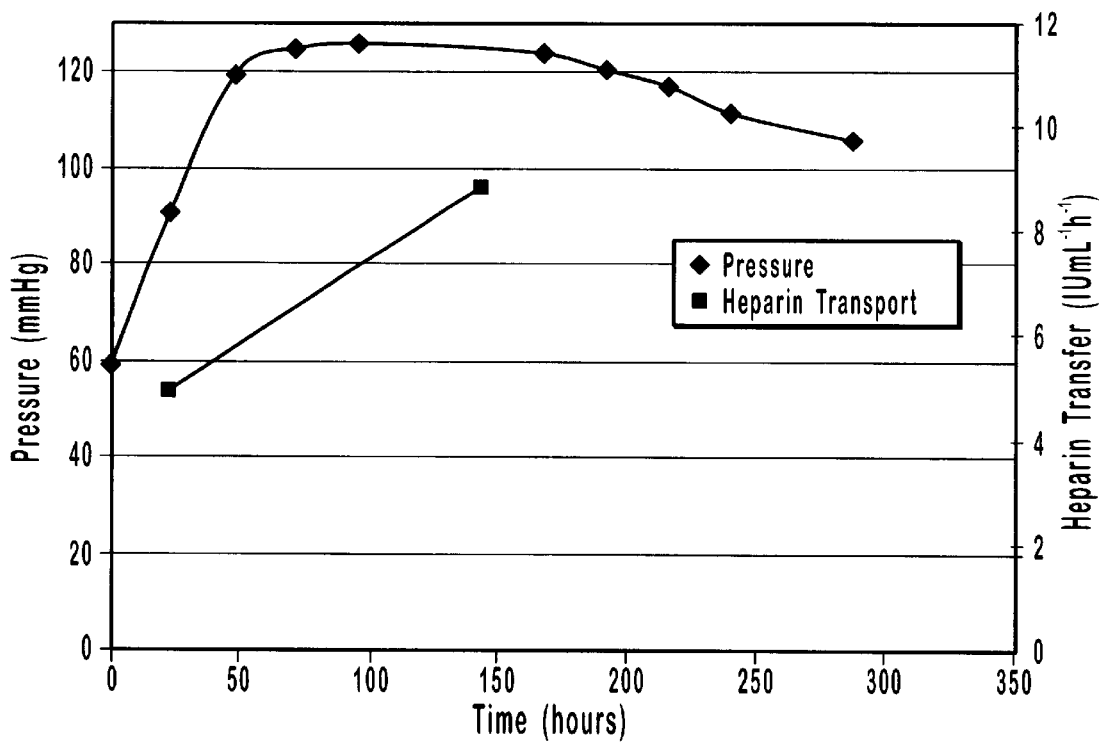
FIG. 12 shows the time evolution of the osmotic pressure and the osmotic pressure and heparin transfer for a heparin aqueous solution with 1% albumin.

FIGS. 11 and 12 show pressure and heparin transfer as a function of time as experienced by an embodiment of a permeable balloon according to the present invention. In these experiments, solutions of heparin were used at concentrations up to about 20000 IU. Solutions of albumin were used at concentrations of up to about 5%. Commercial availability of the respective solutions of heparin and albumin determined the choice of these upper concentration limits.

Osmotic pressures were measured with a pressure transducer. The use of this device instead of liquid column height measurements reduces or even avoids errors that are associated with the use of liquid columns. These errors are typically associated with factors such as solute concentration inhomogeneity problems or frictional problems that can lead to incorrect pressure readings.

Solutions with heparin at different concentrations were used in successive experiments with embodiments of a permeable balloon. In some experiments, the solutions contained albumin, whereas in other experiments no albumin was present. FIGS. 11 and 12 illustrate results obtained in experiments performed with a heparin solution with no albumin (FIG. 11), and with a heparin solution with 1% albumin (FIG. 12). In embodiments with solutions that contained heparin only, the osmotic pressure is due to the heparin that remains in the balloon, whereas in embodiments with heparin and albumin solution, the osmotic pressure is due to the albumin and to the heparin that remains in the balloon. The data shown in FIGS. 11 and 12 were obtained through the use of an apparatus having a balloon with a semipermeable membrane formed from with Millipore® 50, and with 20000 IU/ml heparin solutions.

As shown in FIG. 11, osmotic pressure of almost 80 mmHg was measured shortly after the heparin solution was placed in a permeable balloon. The pressure remained above 80 mmHg for over 150 h, and remained at or about 100 mmHg for at least 120 h. Heparin transfer rates were about 4 IU ml$^{-1}$ h$^{-1}$ one day after the solution was placed in the balloon, and about 7.7 IU ml$^{-1}$ h$^{-1}$ about 170 h after the solution was placed in the balloon.

FIG. 12 shows that a peak pressure of over 120 mmHg was obtained with a solution that contained heparin and 1% albumin. This observation should be expected because in this case albumin, which does not significantly permeate through the membrane, causes osmotic pressure in addition to the heparin that remains within the balloon. Heparin transfer rates were about 5 IU ml$^{-1}$ h$^{-1}$ one day after the solution was placed in the balloon, and almost 11 IU ml$^{-1}$ h$^{-1}$ about 150 h after the solution was placed in the balloon.

These heparin transfer rates are adequate in light of desirable transport rates in the range of about 5 IU ml$^{-1}$ h$^{-1}$ to about 10 IU ml$^{-1}$ h$^{-1}$. These transport rates from a balloon whose volume is about 2 ml lead to the intravenous administration of not more than 500 IU heparin per day, or to the administration of not more than 5000 IU heparin in a ten-day period.

Safety measures, in addition to practical factors, determine the preferred size of embodiments of permeable balloons of this invention. The administration of at most about 20000 IU heparin in a single administration is currently regarded as an acceptable risk. The amount of heparin that would be suddenly delivered upon rupture of a 5 ml balloon right after having been filled with heparin solution at a concentration of 20000 IU/ml would be about 100000 IU. Instead, this amount would be about 20000 IU if a 2 ml balloon were filled with 10000 IU/ml heparin. Consequently, a 2-ml balloon is preferred in most embodiments of permeable balloons.

The transport rates shown in FIGS. 11–12 also indicate each supply of heparin within the balloon can intravenously provide heparin for at least a ten-day period before the balloon is recharged with a fresh supply of heparin. The pressure data shown in the same figures show that sufficiently high pressure can be achieved with embodiments of the present invention because even in unusual conditions the venous pressure does not rise above 50 mmHg.

The foregoing procedure to determine osmotic pressure and concentrations of substances in the fluid filling of an embodiment of an occlusal balloon according to this invention can be properly adapted with ordinary skill in the art to analogously determine the osmotic pressure and adequate concentrations of other substances in the same or in a different type of vascular access.

SUMMARY OF PREFERRED EMBODIMENTS

The elements of the embodiments of this invention disclosed hereinabove, equivalents thereof, and their functionalities can be expressed as means for performing specified functions as described hereinbelow.

Many examples are provided herein of a balloon means for selectively occluding an opening in a blood vessel. Examples of means for selectively occluding an opening according to this invention include: occlusal balloons such as nonpermeable occlusal balloons, occlusal balloons that have an integral permeable region, occlusal balloons with a semipermeable membrane, occlusal balloons with radio-opaque markings, occlusal balloons that are inflated with a liquid, occlusal balloons that are inflated with a gas, and occlusal balloons that are configured to operate in conjunction with or in the presence of at least another occlusal balloon. Occlusal balloon 40 in FIG. 1A illustrates an exemplary embodiment of an impermeable occlusal balloon when delivery end 42 does not essentially allow for significant matter transport. Occlusal balloon 40 in FIG. 1A illustrates an exemplary embodiment of an occlusal balloon with a semipermeable region when delivery end 42 allows for selective matter transport.

Note that each embodiment of the means for selectively occluding an opening according to this invention has a delivery end that is generally located in the region near the anastomosis site and an opposite access end that is typically provided with a connection to the means for selectively providing access to a means for selectively occluding an opening. Each embodiment of a means for selectively occluding an opening in a blood vessel functions according to this invention by adopting a variety of configurations such as a distended configuration and a contracted configuration. In particular, the distended configuration can be an inflated configuration, and the contracted configuration can be a collapsed configuration. Preferably, the distended configuration is adopted when an embodiment of a means for selectively occluding an opening is filled with a liquid, although the fluid filling some of such embodiments can also be a gas. Blood from the accessed vessel cannot infiltrate into the anastomosed graft vessel when the embodiment of the means for selectively occluding an opening is in its distended configuration, whereas fluid communication from the interior of the anastomosed graft vessel into the lumen of the accessed blood vessel is allowed in the contracted configuration of the same embodiment. Any of such specific embodiments is manufactured so that it can change from any one of these particular configurations to the other and vice-versa a plurality of times. The number of times which these changes in configuration are experienced by embodiments of the means for selectively occluding an opening according to this invention can be of the order of the number of injections that a blood vessel would typically be subjected to during a long term treatment of a chronic affliction or during dialysis treatment.

Examples are also provided herein of a means for selectively and controllably exposing blood flow to an agent in a vascular access. Means for selectively and controllably exposing blood flow to an agent according to this invention is embodied by means for selectively effectuating transport of an agent in a vascular access, and by means for selectively subjecting blood flow to contact with an agent. Exemplary embodiments of each one of these means are enumerated in turn below.

Means for selectively effectuating transport of an agent in a vascular access or at an anastomosis site according to this invention is embodied by permeating sources of physiologically active agents or other agents. These permeating sources are more specifically embodied by sources such as a semipermeable membrane attached to an occlusal balloon or a semipermeable region of an occlusal balloon. Occlusal balloons having an integral semipermeable region or an attached semipermeable membrane may be generically referred to as occlusal balloons having a semipermeable portion. Such semipermeable portions are exemplified by semipermeable membranes 43' shown in FIGS. 2A–2B, 43" shown in FIG. 3, and 143a–c shown in FIGS. 5A–5C; sources that include a plurality of semipermeable membranes, exemplified by semipermeable membranes 43a and 43b shown in FIG. 4, semipermeable membranes in any of a mono-layer, bi-layer, tri- or generally multi-layer and sandwiched configurations; sources that include at least a semipermeable membrane with a backing (membrane mounting by backing); sources that include at least a semipermeable membrane braced to an occlusal balloon exemplified by the embodiment shown in FIG. 5C; sources that include at least a semipermeable membrane bonded to an embodiment of means for selectively occluding an opening (membrane mounting by bonding), exemplified by the embodiment shown in FIG. 5B; sources that include at least a semipermeable membrane that is backed by material of an embodiment of means for selectively occluding an opening (membrane mounting by backing) exemplified by the embodiment shown in FIG. 5A; and sources that include a semipermeable region of material of an embodiment of means for selectively occluding an opening, exemplified by the embodiment shown in FIG. 5D, FIG. 1A, FIGS. 7A–7B and FIG. 9. Note that an occlusal balloon having an integral semipermeable region is an example of means for selectively occluding an opening means and for selectively effectuating transport of an agent in a vascular access at an anastomosis site.

Each embodiment of a means for selectively and controllably exposing blood flow to an agent in a vascular access is integrally formed in or attached to the delivery end of an embodiment of a means for selectively occluding an opening according to this invention. The means for selectively and controllably exposing blood flow to an agent in a vascular access functions according to the present invention by exposing the blood flow at the anastomosis site to at least one physiologically active agent, such as a substance that will prevent the formation of blood clots. Means for selectively and controllably subjecting blood flow to contact with an agent according to this invention is embodied by in-situ sources of physiologically active agents and by nonpermeating sources of physiologically active agents.

Many examples are also provided herein of a means for selectively providing access to a means for selectively occluding an opening in a blood vessel. Examples of means for selectively providing access to a means for selectively occluding an opening in a blood vessel include: port devices such as a port device with one self-sealing access cavity, such as port devices 50 shown in FIG. 1A, 50" shown in FIG. 1C, port device 50' shown in FIGS. 2A–2B, a port device with a plurality of self-sealing access cavities, such as port device 50ab shown in FIG. 4, port device 250 shown in FIGS. 7A–7B, coupler port 350 and a port device that includes ports for providing conduits to operate probes, sampling devices, imaging Each embodiment of the means for selectively providing access to a means for selectively occluding an opening facilitates the external introduction into or the extraction from a specific embodiment of the means for selectively occluding an opening of fluid therein contained. In particular, an embodiment of the means for selectively providing access to a means for selectively occluding an opening is adapted for a subcutaneous placement and it is provided with at least one self-sealing cavity or valve for selectively allowing fluid communication through a conduit into the access end of an embodiment of a means for selectively occluding an opening in a blood vessel.

The anastomosed graft of this invention may provide physical support to a particular embodiment of the means for selectively occluding an opening and to a particular embodiment of the means for selectively providing access to a means for selectively occluding an opening. In preferred embodiments, this support is provided by a housing such that the anastomosed graft contains in its interior an embodiment of a means for selectively occluding an opening. The graft vessels are examples of means for an anastomosed vascular access with a blood vessel.

One of the ends of the anastomosed graft of this invention is anastomosed to the vessel being accessed. The opposite end of the anastomosed graft may be integrally or detachably connected to an embodiment of means for providing access to a means for selectively occluding an opening.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A vascular access system for facilitating repeated access to a blood vessel, the apparatus comprising:
    (a) a graft vessel means for providing a fluid conduit, the graft vessel means having an anastomosis end and an opposite port end, the graft vessel means being adapted for anastomosis at its anastomosis end with a blood vessel;
    (b) means for selectively occluding an opening in a blood vessel at the anastomosis end of the graft vessel means, said occluding means being positioned at the anastomosis end of the graft vessel means, said occluding means being adapted for distension and contraction at the anastomosis end of the graft vessel means to enable the occluding means to block fluid communication between the graft vessel means and a blood vessel when expanded in a distended position and to permit fluid communication between the graft vessel means and the blood vessel when contracted to a contracted position; and
    (c) means for selectively providing access to the occluding means, the means for selectively providing access being attached in a leak proof manner to the occluding means to provide fluid communication, the means for selectively providing access being configured to remain within a patient's body after anastomosis of the graft vessel means to the blood vessel while being accessible from outside of the patient's body to deliver and withdraw fluids and cause selective distension and contraction of the occluding means.

2. A vascular access system as recited in claim 1, wherein said means for selectively occluding an opening includes at least one occlusal balloon.

3. A vascular access system as recited in claim 2, wherein said occlusal balloon is an impermeable balloon that prevents significant transport of matter from the interior of said occlusal balloon to the interior of the blood vessel.

4. A vascular access system as recited in claim 1, wherein said means for selectively occluding an opening in a blood vessel at the anastomosis end of the graft vessel means further comprises:
    means for selectively and controllably exposing blood flow in the blood vessel to at least one physiologically active agent at a delivery end of the means for selectively occluding an opening.

5. A vascular access system as recited in claim 4, wherein said means for selectively and controllably exposing blood flow in the blood vessel is integrally formed to the delivery end of said means for selectively occluding an opening.

6. A vascular access system as recited in claim 4, wherein said means for selectively and controllably exposing blood flow in the blood vessel includes a semipermeable region of said balloon means.

7. A vascular access system as recited in claim 4, wherein said means for selectively and controllably exposing blood flow in the blood vessel is attached to the delivery end of said balloon means.

8. A vascular access system as recited in claim 4, wherein said means for selectively and controllably exposing blood flow in the blood vessel comprises means for selectively effectuating transport of agent in the vascular access.

9. A vascular access system as recited in claim 4, wherein said means for selectively and controllably exposing blood flow in the blood vessel comprises at least one semipermeable membrane.

10. A vascular access system as recited in claim 4, wherein said means for selectively and controllably exposing blood flow in the blood vessel comprises means for selectively subjecting blood flow to contact with an agent.

11. A vascular access system for facilitating repeated access to a blood vessel, the apparatus comprising:
(a) a graft vessel with an anastomosis end and an opposite port end, the graft vessel being adapted for anastomosis at its anastomosis end with a blood vessel;
(b) an occlusal balloon having an interior capable of receiving a fluid, said occlusal balloon being positioned and adapted for distension and contraction to enable the occlusal balloon to block fluid communication between the graft vessel and the blood vessel at the anastomosis en of the graft vessel when the occlusal balloon is expanded in a distended position and to permit fluid communication between the graft vessel and the blood vessel when contract to a contracted position; and
(c) a port device attached in a leak proof manner to the occlusal balloon to provide fluid communication, the port device being configured to remain within a patient's body after anastomosis of the graft vessel to the blood vessel while being accessible from outside of the patient's body to deliver and withdraw fluids and cause selective distension and contraction of the occlusal balloon.

12. A vascular access system as recited in claim 11, wherein said occlusal balloon is an impermeable occlusal balloon that prevents significant transport of matter from the interior of said occlusal balloon to the interior of the blood vessel.

13. A vascular access system as recited in claim 11, further comprising
a semipermeable membrane at a delivery end of the occlusal balloon adapted to allow selective matter transport between the blood in the blood vessel and the interior of the occlusal balloon.

14. A vascular access system as recited in claim 11, further comprising
a semipermeable region that is integrally formed at a delivery end of said occlusal balloon and that is adapted to selectively and controllably expose blood flow in the blood vessel to at least one physiologically active agent at the delivery end of the occlusal balloon.

15. A vascular access system as recited in claim 11, further comprising means for selectively subjecting blood flow in the blood vessel to contact with at least one physiologically active agent at a delivery end of the occlusal balloon.

16. A vascular access apparatus for facilitating repeated access to a blood vessel, comprising:
(a) a graft vessel means for providing a fluid conduit, the graft vessel means having an anastomosis end d an opposite port end, the graft vessel being adapted for anastomosis at its anastomosis end with a blood vessel;
(b) means for selectively occluding an opening at the anastomosis end, said occluding means extending integrally from the graft vessel, said occluding means being positioned and adapted for distension and contraction in a manner that enables the occluding means to block fluid communication between the graft vessel means and a blood vessel at the anastomosis end of the graft vessel when the occluding means is expanded in a distended position and that permits fluid communication between the graft vessel and the blood vessel hen contracted to a contracted position; and
(c) means for selectively providing access to the occluding means, the means for selectively providing access being attached in a leak proof manner to the occluding means to provide fluid communication, the means for selectively providing access being configured to remain within a patient's body after anastomosis of the graft vessel means to a blood vessel while being accessible from outside of the patient's body to deliver and withdraw fluids and cause elective distention and contraction of the occluding means.

17. A vascular access apparatus as recited in claim 16, wherein said means for selectively occluding opening is an occlusal balloon.

18. A vascular access apparatus as recited in claim 17, wherein said occlusal balloon is an impermeable occlusal balloon that prevents significant transport of matter from the interior of said occlusal balloon to the interior of the blood vessel.

19. A vascular access apparatus as recited in claim 16, wherein said means for selectively providing access is a port device.

20. A vascular access apparatus as recited in claim 19, wherein said port device has at least one self-sealing cavity.

21. A vascular access apparatus as recited in claim 19, wherein said port device is provided with at least one port for delivery of a liquid or a gas.

22. A vascular access apparatus as recited in claim 16, further comprising means for selectively and controllably exposing blood flow in the blood vessel to at least one physiologically active agent at a delivery end of the means for selectively occluding an opening.

23. A vascular access apparatus as recited in claim 22, wherein said means for selectively and controllably exposing blood flow in the blood vessel is integrally formed into the delivery end of said means for selectively occluding an opening.

24. A vascular access apparatus as recited in claim 22, wherein said means for selectively and controllably exposing blood flow in the blood vessel is attached to the delivery end of said means for selectively occluding an opening.

25. A vascular access apparatus as recited in claim 22, wherein said means for selectively and controllably exposing blood flow in the blood vessel is a means for selectively subjecting blood flow to contact with an agent.

26. A vascular access apparatus for facilitating repeated access to a blood vessel, comprising:
(a) a graft vessel with an anastomosis end and an opposite port end, the anastomosis end of the graft vessel being adapted for anastomosis to a blood vessel;
(b) an occlusal balloon having an interior capable of receiving a fluid, the occlusal balloon extending integrally from the graft vessel, said occlusal balloon being positioned and adapted for distension and contraction in a manner that enables the occlusal balloon to block fluid communication between the graft vessel and a blood vessel at the anastomosis end of the graft vessel when the occlusal balloon is expanded in a distended position that permits fluid communication between the graft vessel and the blood vessel when contracted to a contracted position; and (c) a port device attached in a leak proof manner to the occlusal balloon to provide fluid communication, the port device being configured to remain within a patient's body after anastomosis of the graft vessel to the blood vessel while being accessible from outside of the patient's body to deliver and withdraw fluids and cause selective distension and contraction of the occlusal balloon.

27. A vascular access apparatus as recited in claim 26, wherein said occlusal balloon is an impermeable occlusal balloon that prevents significant transport of matter from the interior of said occlusal balloon to the interior of the blood vessel.

28. A vascular access apparatus as recited in claim 26, wherein said port device has at least one self-sealing cavity.

29. A vascular access apparatus as recited in claim 26, wherein said port device is provided with at least one port for delivery of a liquid or a gas.

30. A vascular access apparatus as recited in claim 26, further comprising a semipermeable membrane at the delivery end of the occlusal balloon adapted to allow selective matter transport between the blood in the blood vessel and the interior of the occlusal balloon.

31. A vascular access apparatus as recited in claim 26, further comprising a semipermeable region at the delivery end of the occlusal balloon adapted to allow selective matter transport between the blood in the blood vessel and the interior of the occlusal balloon.

32. A vascular access apparatus for facilitating repeated access to a blood vessel, comprising:

(a) a graft vessel with an anastomosis end and an opposite port end, wherein the port end is sealed to prevent fluid in the graft vessel from leaking at the port end, and wherein the anastomosis end of the graft vessel is adapted for anastomosis to a blood vessel;

(b) an occlusal balloon having an interior capable of receiving a fluid, said occlusal balloon being positioned and adapted for distension and contraction in a manner that enables the occlusal balloon to block fluid communication between the graft vessel and a blood vessel at the anastomosis end of the graft vessel when the occlusal balloon is expanded in a distended position and that permits fluid communication between the graft vessel and the blood vessel when contracted to a contracted position; and (c) a port device attached in a leak proof manner to the occlusal balloon to provide fluid communication, the port device being configured to remain within a patient's body after anastomosis of the graft vessel to the blood vessel while being accessible from outside of the patient's body to deliver and withdraw fluids and cause selective distension and contraction of the occlusal balloon.

33. The apparatus of claim 32, wherein a stop is positioned at the port end of the graft vessel to seal the graft vessel at the port end.

34. The apparatus of claim 32, wherein the port end of the graft vessel is at least partially sealed by the port device.

35. A vascular access apparatus for facilitating repeated access to a blood vessel, comprising:

(a) a graft vessel with an anastomosis end and an opposite port end, the anastomosis end of the graft vessel being adapted for anastomosis to a blood vessel;

(b) an occlusal balloon having an interior capable of receiving a fluid, said occlusal balloon being positioned and adapted for distension and contraction in a manner that enables the occlusal balloon to block fluid communication between the graft vessel and a blood vessel at the anastomosis end of the graft vessel when the occlusal balloon is expanded in a distended position and that permits fluid communication between the graft vessel and the blood vessel when contracted to a contracted position; and (c) a port device attached in a leak proof manner to the occlusal balloon via a coupling tube to provide fluid communication, the port device being configured to remain within a patient's body after anastomosis of the graft vessel to the blood vessel while being accessible from outside of the patient's body to deliver and withdraw fluids and cause selective distension and contraction of the occlusal balloon.

36. The apparatus of claim 35, wherein the coupling tube extends into the graft vessel.

37. The apparatus claim 35, wherein the coupling tube extends in the graft vessel.

* * * * *

UNITED STATES PATENT AND TRADEMARK OFFICE
CERTIFICATE OF CORRECTION

PATENT NO. : 6,663,590 B2
APPLICATION NO. : 09/760322
DATED : December 16, 2003
INVENTOR(S) : Blatter et al.

It is certified that error appears in the above-identified patent and that said Letters Patent is hereby corrected as shown below:

Column 2, line 38, "...typically ranges form about 2 years..." change to --typically ranges from about 2 years--.

Column 3, line 11, "...devices that come an occlusal..." change to --devices that comprise an occlusal--

Column 11, line 4, "...material that has a can be utilized..." change to --material that can be utilized--

Column 29, line 27, "en of the graft vessel..." change to --end of the graft vessel--

Column 29, line 65, "...an anastomosis end d an" change to --an anastomosis end and an--

Column 30, line 10, "...and the blood vessel hen" change to --and the blood vessel when--

Column 30, line 20, "...and cause elective distention and..." change to --and cause selective distention and--

Column 30, line 23, "...selectively occluding opening is..." change to --selectively occluding an opening is--

Signed and Sealed this

Eighth Day of April, 2008

JON W. DUDAS
*Director of the United States Patent and Trademark Office*